(12) United States Patent
Bruenker et al.

(10) Patent No.: US 9,975,958 B2
(45) Date of Patent: May 22, 2018

(54) TRIMERIC ANTIGEN BINDING MOLECULES

(71) Applicant: Hoffmann-La Roche Inc., Little Falls, NJ (US)

(72) Inventors: Peter Bruenker, Hittnau (CH); Claudia Ferrara Koller, Zug (CH); Sandra Grau-Richards, Birmensdorf ZH (CH); Ekkehard Moessner, Kreuzlingen (CH); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 148 days.

(21) Appl. No.: 14/934,639

(22) Filed: Nov. 6, 2015

(65) Prior Publication Data

US 2016/0159917 A1    Jun. 9, 2016

Related U.S. Application Data

(63) Continuation of application No. PCT/EP2014/059030, filed on May 5, 2014.

(30) Foreign Application Priority Data

May 7, 2013  (EP) .................................... 13166793

(51) Int. Cl.
    C07K 16/28  (2006.01)
    C07K 16/40  (2006.01)
    C07K 14/78  (2006.01)

(52) U.S. Cl.
    CPC .......... *C07K 16/2878* (2013.01); *C07K 14/78* (2013.01); *C07K 16/40* (2013.01); *C07K 2317/31* (2013.01); *C07K 2317/35* (2013.01); *C07K 2317/55* (2013.01); *C07K 2317/66* (2013.01); *C07K 2317/73* (2013.01); *C07K 2317/92* (2013.01); *C07K 2319/35* (2013.01); *C07K 2319/70* (2013.01); *C07K 2319/74* (2013.01)

(58) Field of Classification Search
    CPC ..... C07K 16/2878; C07K 14/78; C07K 16/40
    See application file for complete search history.

(56) References Cited

U.S. PATENT DOCUMENTS

2004/0033511 A1    2/2004    Pfizenmaier et al.

FOREIGN PATENT DOCUMENTS

| AU | 2011265482 | 1/2012 |
|---|---|---|
| EP | 1 958 959 | 8/2008 |
| WO | 2012/130471 A1 | 10/2012 |
| WO | 2012/140627 A1 | 10/2012 |

OTHER PUBLICATIONS

International Preliminary Report on Patentability for App. Ser. No. PCT/EP2014/059030, dated Aug. 7, 2014, 6 pages.
Allen et al., "Targeting TRAIL Death Receptor 4 with Trivalent DR4 Atrimer Complexes" *Molecular Cancer Therapeutics* 11(10):2087-2095 (Jul. 16, 2012).
Blanco-Toribio et al., "Generation and characterization of monospecific and bispecific hexavalent trimerbodies" *mAbs* 5(1):70-79 (2013).
Boudko et al., "Crystal Structure of Human Collagen XVIII Trimerization" *J Mol Biol* 392:787-802 (2009).
Chames et al. *Engineering: Methods and Protocols, Methods in Molecular Biology*"Chapter 33—Production, purification, and characterization of scFv TNF ligand fusion proteins" Patrick Chames, Second edition,Humana Press, vol. 907:597-609 (2012).
Crothers et al., "The influence of polyvalency on the binding properties of antibodies" *Immunochemistry* 9:341-357 (Jan. 15, 1971).
Cuesta et al., "Improved stability of multivalent antibodies containing the human collagen XV trimerization domain" *mAbs* 4(2):226-232 (2012).
Deyev et al., "Multivalency: the hallmark of antibodies used for optimization of tumor targeting by design" *BioEssays* 30:904-918 (2008).
Kashentseva et al., "Adenovirus Targeting to c-erbB-2 Oncoprotein by Single-Chain Antibody Fused to Trimeric Form of Adenovirus Receptor Ectodomain" *Cancer Research* 62:609-616 (Jan. 15, 2002).
Kim et al., "Heptameric Targeting Ligands against EGFR and HER2 with High Stability and Avidity" *PLOS One* 7(8):e43077 (2012).
Kim et al., "Tribody: Robust self-assembled trimeric targeting ligands with high stability and significantly improved target-binding strength" *Biochemistry* 52(41):7283-7294 (Sep. 15, 2013).
Kortt et al., "Dimeric and trimeric antibodies: high avidity scFvs for cancer targeting" *Biomolecular Engineering* 18(3):95-108 (2001).
Krammer et al., "A Carboxy-Terminal Trimerization Domain Stabilizes Conformational Epitopes on the Stalk Domain of Soluble Recombinant Hemagglutinin Substrates" *PLOS One* 7(8):e43603 (2012).
Lee et al., "Bivalent antibody phage display mimics natural immunoglobulin" Journal of *Immunological Methods* 284:119-132 (2004).
Li et al., "Chemically Self-Assembled Antibody Nanorings (CSANs): Design and Characterization of an Anti-CD3 IgM Biomimetic"*JACS Articles* 132(48):17247-17257 (2010).
Pluckthun et al., "New protein engineering approaches to multivalent and bispecific antibody fragments" *Immunotechnology* 3:83-105 (1997).
Saha et al., "Designed cyclic permutants of HIV-1 gp120: implications for envelope trimer structure and immunogen design" *Biochemistry* 51(9):1836-1847 (Mar. 6, 2012).

(Continued)

*Primary Examiner* — Prema Mertz
(74) *Attorney, Agent, or Firm* — Anna M. Tan

(57) ABSTRACT

The present invention pertains to a trimeric antigen binding molecule comprising three fusion polypeptides, each comprising at least one antigen binding moiety fused to a trimerization domain derived from human cartilage matrix protein. In addition, the present invention relates to polynucleotides encoding such trimeric antigen binding molecules, and vectors and host cells comprising such polynucleotides. The invention further relates to methods for producing the trimeric antigen binding molecules of the invention, and to methods of using these trimeric antigen binding molecules in the treatment of disease.

23 Claims, 5 Drawing Sheets

(56) References Cited

OTHER PUBLICATIONS

Shu et al., "Trimerization Specificity in HIV-1 gp41:Analysis with a GCN4 Leucine Zipper Model" *Biochemistry* 38:5378-5385 (1999).
Stone et al., "The assembly of single domain antibodies into bispecific decavalent molecules" *Journal of Immunological Methods* 318(1-2):88-94 (2007).
Terskikh et al., ""Peptabody": A new type of high avidity binding protein" Proc. *Natl. Sci. USA* 94:1663-1668 (1997).
Wirz et al., "Crystal structure of the human collagen XV trimerization domain A potent trimerizing unit common to multiplexin collagens" *Matrix Biology* 30:9-15 (2011).
Wyzgol et al., "Trimer Stabilization, Oligomerization, and Antibody-Mediated Cell Surface, Immobilization Improve the Activity of Soluble Trimers of CD27L, CD40L, 41BBL, and Glucocorticoid-Induced TNF Receptor Ligand1" *The Journal of Immunology* 183:1851-1861 (2009).
Zhu et al., "COMBODY: one-domain antibody multimer with improved avidity" *Immunology and Cell Biology* 88(6):667-675 (Mar. 9, 2010).

SEQUENCE LISTING

<160> NUMBER OF SEQ ID NOS: 22

<210> SEQ ID NO 1
<211> LENGTH: 496
<212> TYPE: PRT
<213> ORGANISM: Artificial sequence
<220> FEATURE:
<223> OTHER INFORMATION: Full length human CMP

<400> SEQUENCE: 1

```
Met Arg Val Leu Ser Gly Thr Ser Leu Met Leu Cys Ser Leu Leu Leu
1               5                   10                  15

Leu Leu Gln Ala Leu Cys Ser Pro Gly Leu Ala Pro Gln Ser Arg Gly
            20                  25                  30

His Leu Cys Arg Thr Arg Pro Thr Asp Leu Val Phe Val Val Asp Ser
        35                  40                  45

Ser Arg Ser Val Arg Pro Val Glu Phe Glu Lys Val Lys Val Phe Leu
    50                  55                  60

Ser Gln Val Ile Glu Ser Leu Asp Val Gly Pro Asn Ala Thr Arg Val
65                  70                  75                  80

Gly Met Val Asn Tyr Ala Ser Thr Val Lys Gln Glu Phe Ser Leu Arg
                85                  90                  95

Ala His Val Ser Lys Ala Ala Leu Leu Gln Ala Val Arg Arg Ile Gln
            100                 105                 110

Pro Leu Ser Thr Gly Thr Met Thr Gly Leu Ala Ile Gln Phe Ala Ile
        115                 120                 125

Thr Lys Ala Phe Gly Asp Ala Glu Gly Gly Arg Ser Arg Ser Pro Asp
    130                 135                 140

Ile Ser Lys Val Val Ile Val Val Thr Asp Gly Arg Pro Gln Asp Ser
145                 150                 155                 160

Val Gln Asp Val Ser Ala Arg Ala Arg Ala Ser Gly Val Glu Leu Phe
                165                 170                 175

Ala Ile Gly Val Gly Ser Val Asp Lys Ala Thr Leu Arg Gln Ile Ala
            180                 185                 190

Ser Glu Pro Gln Asp Glu His Val Asp Tyr Val Glu Ser Tyr Ser Val
        195                 200                 205

Ile Glu Lys Leu Ser Arg Lys Phe Gln Glu Ala Phe Cys Val Val Ser
    210                 215                 220

Asp Leu Cys Ala Thr Gly Asp His Asp Cys Glu Gln Val Cys Ile Ser
225                 230                 235                 240

Ser Pro Gly Ser Tyr Thr Cys Ala Cys His Glu Gly Phe Thr Leu Asn
                245                 250                 255

Ser Asp Gly Lys Thr Cys Asn Val Cys Ser Gly Gly Gly Ser Ser
            260                 265                 270

Ala Thr Asp Leu Val Phe Leu Ile Asp Gly Ser Lys Ser Val Arg Pro
        275                 280                 285

Glu Asn Phe Glu Leu Val Lys Lys Phe Ile Ser Gln Ile Val Asp Thr
    290                 295                 300

Leu Asp Val Ser Asp Lys Leu Ala Gln Val Gly Leu Val Gln Tyr Ser
```

```
                305                 310                 315                 320
Ser Ser Val Arg Gln Glu Phe Pro Leu Gly Arg Phe His Thr Lys Lys
                    325                 330                 335

Asp Ile Lys Ala Ala Val Arg Asn Met Ser Tyr Met Glu Lys Gly Thr
                340                 345                 350

Met Thr Gly Ala Ala Leu Lys Tyr Leu Ile Asp Asn Ser Phe Thr Val
            355                 360                 365

Ser Ser Gly Ala Arg Pro Gly Ala Gln Lys Val Gly Ile Val Phe Thr
        370                 375                 380

Asp Gly Arg Ser Gln Asp Tyr Ile Asn Asp Ala Ala Lys Lys Ala Lys
385                 390                 395                 400

Asp Leu Gly Phe Lys Met Phe Ala Val Gly Val Gly Asn Ala Val Glu
                405                 410                 415

Asp Glu Leu Arg Glu Ile Ala Ser Glu Pro Val Ala Glu His Tyr Phe
            420                 425                 430

Tyr Thr Ala Asp Phe Lys Thr Ile Asn Gln Ile Gly Lys Lys Leu Gln
        435                 440                 445

Lys Lys Ile Cys Val Glu Glu Asp Pro Cys Ala Cys Glu Ser Leu Val
450                 455                 460

Lys Phe Gln Ala Lys Val Glu Gly Leu Leu Gln Ala Leu Thr Arg Lys
465                 470                 475                 480

Leu Glu Ala Val Ser Lys Arg Leu Ala Ile Leu Glu Asn Thr Val Val
                485                 490                 495

<210> SEQ ID NO 2
<211> LENGTH: 39
<212> TYPE: PRT
<213> ORGANISM: Artificial sequence
<220> FEATURE:
<223> OTHER INFORMATION: CMP trimerization domain

<400> SEQUENCE: 2

Cys Ala Cys Glu Ser Leu Val Lys Phe Gln Ala Lys Val Glu Gly Leu
1               5                   10                  15

Leu Gln Ala Leu Thr Arg Lys Leu Glu Ala Val Ser Lys Arg Leu Ala
            20                  25                  30

Ile Leu Glu Asn Thr Val Val
        35

<210> SEQ ID NO 3
<211> LENGTH: 308
<212> TYPE: PRT
<213> ORGANISM: Artificial sequence
<220> FEATURE:
<223> OTHER INFORMATION: VHCH1-CMP-Flag DR5 clone 2A11

<400> SEQUENCE: 3

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80
```

-continued

```
Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Pro Tyr Gly Arg Tyr Ala Ala Leu Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Gly Gly Gly Gly Ser Gly Gly Gly Ser Glu Glu Asp
                245                 250                 255

Pro Cys Ala Cys Glu Ser Leu Val Lys Phe Gln Ala Lys Val Glu Gly
                260                 265                 270

Leu Leu Gln Ala Leu Thr Arg Lys Leu Glu Ala Val Ser Lys Arg Leu
            275                 280                 285

Ala Ile Leu Glu Asn Thr Val Val Ala Ser Asp Tyr Lys Asp Asp Asp
290                 295                 300

Asp Lys Ser Gly
305
```

<210> SEQ ID NO 4
<211> LENGTH: 305
<212> TYPE: PRT
<213> ORGANISM: Artificial sequence
<220> FEATURE:
<223> OTHER INFORMATION: VHCH1-CMP-Flag DR5 clone 5E11

<400> SEQUENCE: 4

```
Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gly Val Arg Val Ser Phe Asp Tyr Trp Gly Gln
        115                 120                 125
```

```
Gly Thr Leu Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Ser Leu Gly Thr Gln Thr Tyr Ile Cys Asn Val Asn His Lys
        210                 215                 220

Pro Ser Asn Thr Lys Val Asp Lys Lys Val Glu Pro Lys Ser Cys Asp
225                 230                 235                 240

Gly Gly Gly Gly Ser Gly Gly Gly Ser Glu Glu Asp Pro Cys Ala
                245                 250                 255

Cys Glu Ser Leu Val Lys Phe Gln Ala Lys Val Glu Gly Leu Leu Gln
                260                 265                 270

Ala Leu Thr Arg Lys Leu Glu Ala Val Ser Lys Arg Leu Ala Ile Leu
            275                 280                 285

Glu Asn Thr Val Val Ala Ser Asp Tyr Lys Asp Asp Asp Asp Lys Ser
        290                 295                 300

Gly
305

<210> SEQ ID NO 5
<211> LENGTH: 528
<212> TYPE: PRT
<213> ORGANISM: Artificial sequence
<220> FEATURE:
<223> OTHER INFORMATION: DR5 (5E11) Fab molecule- CMP-_FAP(28H1)CrossFab

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

```
Ser Gly Leu Tyr Ser Leu Ser Ser Val Val Thr Val Pro Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Gly Gly Gly
    210                 215                 220

Gly Ser Gly Gly Gly Gly Ser Glu Glu Asp Pro Cys Ala Cys Glu Ser
225                 230                 235                 240

Leu Val Lys Phe Gln Ala Lys Val Glu Gly Leu Leu Gln Ala Leu Thr
                245                 250                 255

Arg Lys Leu Glu Ala Val Ser Lys Arg Leu Ala Ile Leu Glu Asn Thr
            260                 265                 270

Val Val Ala Ser Asp Tyr Lys Asp Asp Asp Lys Ser Gly Gly Gly
        275                 280                 285

Gly Ser Gly Gly Gly Gly Ser Gly Gly Gly Ser Gly Gly Gly Gly
    290                 295                 300

Ser Glu Val Gln Leu Leu Glu Ser Gly Gly Gly Leu Val Gln Pro Gly
305                 310                 315                 320

Gly Ser Leu Arg Leu Ser Cys Ala Ala Ser Gly Phe Thr Phe Ser Ser
                325                 330                 335

His Ala Met Ser Trp Val Arg Gln Ala Pro Gly Lys Gly Leu Glu Trp
            340                 345                 350

Val Ser Ala Ile Trp Ala Ser Gly Glu Gln Tyr Tyr Ala Asp Ser Val
        355                 360                 365

Lys Gly Arg Phe Thr Ile Ser Arg Asp Asn Ser Lys Asn Thr Leu Tyr
    370                 375                 380

Leu Gln Met Asn Ser Leu Arg Ala Glu Asp Thr Ala Val Tyr Tyr Cys
385                 390                 395                 400

Ala Lys Gly Trp Leu Gly Asn Phe Asp Tyr Trp Gly Gln Gly Thr Leu
                405                 410                 415

Val Thr Val Ser Ser Ala Ser Val Ala Ala Pro Ser Val Phe Ile Phe
            420                 425                 430

Pro Pro Ser Asp Glu Gln Leu Lys Ser Gly Thr Ala Ser Val Val Cys
        435                 440                 445

Leu Leu Asn Asn Phe Tyr Pro Arg Glu Ala Lys Val Gln Trp Lys Val
    450                 455                 460

Asp Asn Ala Leu Gln Ser Gly Asn Ser Gln Glu Ser Val Thr Glu Gln
465                 470                 475                 480

Asp Ser Lys Asp Ser Thr Tyr Ser Leu Ser Ser Thr Leu Thr Leu Ser
                485                 490                 495

Lys Ala Asp Tyr Glu Lys His Lys Val Tyr Ala Cys Glu Val Thr His
            500                 505                 510

Gln Gly Leu Ser Ser Pro Val Thr Lys Ser Phe Asn Arg Gly Glu Cys
        515                 520                 525

<210> SEQ ID NO 6
<211> LENGTH: 289
<212> TYPE: PRT
<213> ORGANISM: Artificial sequence
<220> FEATURE:
<223> OTHER INFORMATION: DR5 (5E11) Fab molecule- CMP-_FAP(28H1) scFv
      VHCH1-CMP-VHVL

<400> SEQUENCE: 6

Gly Ser Glu Glu Asp Pro Cys Ala Cys Glu Ser Leu Val Lys Phe Gln
1               5                   10                  15
```

```
Ala Lys Val Glu Gly Leu Leu Gln Ala Leu Thr Arg Lys Leu Glu Ala
             20                  25                  30

Val Ser Lys Arg Leu Ala Ile Leu Glu Asn Thr Val Ser Gly Gly
         35                  40                  45

Gly Gly Ser Gly Gly Gly Ser Gly Gly Gly Ser Gly Gly Gly
 50                  55                  60

Gly Ser Glu Val Gln Leu Leu Glu Ser Gly Gly Gly Leu Val Gln Pro
 65                  70                  75                  80

Gly Gly Ser Leu Arg Leu Ser Cys Ala Ala Ser Gly Phe Thr Phe Ser
                 85                  90                  95

Ser His Ala Met Ser Trp Val Arg Gln Ala Pro Gly Lys Gly Leu Glu
                100                 105                 110

Trp Val Ser Ala Ile Trp Ala Ser Gly Glu Gln Tyr Tyr Ala Asp Ser
                115                 120                 125

Val Lys Gly Arg Phe Thr Ile Ser Arg Asp Asn Ser Lys Asn Thr Leu
130                 135                 140

Tyr Leu Gln Met Asn Ser Leu Arg Ala Glu Asp Thr Ala Val Tyr Tyr
145                 150                 155                 160

Cys Ala Lys Gly Trp Leu Gly Asn Phe Asp Tyr Trp Gly Gln Gly Thr
                165                 170                 175

Leu Val Thr Val Ser Ser Ala Ser Val Ala Ala Pro Ser Val Phe Ile
                180                 185                 190

Phe Pro Pro Ser Asp Glu Gln Leu Lys Ser Gly Thr Ala Ser Val Val
            195                 200                 205

Cys Leu Leu Asn Asn Phe Tyr Pro Arg Glu Ala Lys Val Gln Trp Lys
            210                 215                 220

Val Asp Asn Ala Leu Gln Ser Gly Asn Ser Gln Glu Ser Val Thr Glu
225                 230                 235                 240

Gln Asp Ser Lys Asp Ser Thr Tyr Ser Leu Ser Ser Thr Leu Thr Leu
                245                 250                 255

Ser Lys Ala Asp Tyr Glu Lys His Lys Val Tyr Ala Cys Glu Val Thr
            260                 265                 270

His Gln Gly Leu Ser Ser Pro Val Thr Lys Ser Phe Asn Arg Gly Glu
        275                 280                 285

Cys

<210> SEQ ID NO 7
<211> LENGTH: 289
<212> TYPE: PRT
<213> ORGANISM: Artificial sequence
<220> FEATURE:
<223> OTHER INFORMATION: CMP-FAP(28H1) CrossFab

<400> SEQUENCE: 7

Gly Ser Glu Glu Asp Pro Cys Ala Cys Glu Ser Leu Val Lys Phe Gln
1               5                   10                  15

Ala Lys Val Glu Gly Leu Leu Gln Ala Leu Thr Arg Lys Leu Glu Ala
             20                  25                  30

Val Ser Lys Arg Leu Ala Ile Leu Glu Asn Thr Val Ser Gly Gly
         35                  40                  45

Gly Gly Ser Gly Gly Gly Ser Gly Gly Gly Ser Gly Gly Gly
 50                  55                  60

Gly Ser Glu Val Gln Leu Leu Glu Ser Gly Gly Gly Leu Val Gln Pro
 65                  70                  75                  80
```

```
Gly Gly Ser Leu Arg Leu Ser Cys Ala Ala Ser Gly Phe Thr Phe Ser
            85                  90                  95

Ser His Ala Met Ser Trp Val Arg Gln Ala Pro Gly Lys Gly Leu Glu
        100                 105                 110

Trp Val Ser Ala Ile Trp Ala Ser Gly Glu Gln Tyr Tyr Ala Asp Ser
    115                 120                 125

Val Lys Gly Arg Phe Thr Ile Ser Arg Asp Asn Ser Lys Asn Thr Leu
130                 135                 140

Tyr Leu Gln Met Asn Ser Leu Arg Ala Glu Asp Thr Ala Val Tyr Tyr
145                 150                 155                 160

Cys Ala Lys Gly Trp Leu Gly Asn Phe Asp Tyr Trp Gly Gln Gly Thr
                165                 170                 175

Leu Val Thr Val Ser Ser Ala Ser Val Ala Ala Pro Ser Val Phe Ile
            180                 185                 190

Phe Pro Pro Ser Asp Glu Gln Leu Lys Ser Gly Thr Ala Ser Val Val
        195                 200                 205

Cys Leu Leu Asn Asn Phe Tyr Pro Arg Glu Ala Lys Val Gln Trp Lys
    210                 215                 220

Val Asp Asn Ala Leu Gln Ser Gly Asn Ser Gln Glu Ser Val Thr Glu
225                 230                 235                 240

Gln Asp Ser Lys Asp Ser Thr Tyr Ser Leu Ser Ser Thr Leu Thr Leu
                245                 250                 255

Ser Lys Ala Asp Tyr Glu Lys His Lys Val Tyr Ala Cys Glu Val Thr
            260                 265                 270

His Gln Gly Leu Ser Ser Pro Val Thr Lys Ser Phe Asn Arg Gly Glu
        275                 280                 285

Cys

<210> SEQ ID NO 8
<211> LENGTH: 233
<212> TYPE: PRT
<213> ORGANISM: Artificial sequence
<220> FEATURE:
<223> OTHER INFORMATION: VLCL DR5 clone 2A11

<400> SEQUENCE: 8

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Ser Gln Gly Ile
        35                  40                  45

Arg Asn Tyr Leu Asn Trp Tyr Gln Gln Lys Pro Gly Lys Ala Pro Lys
    50                  55                  60

Leu Leu Ile Tyr Tyr Thr Ser Ser Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Lys
            100                 105                 110

Leu Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
```

```
                145                 150                 155                 160
Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
                210                 215                 220

Thr Lys Ser Phe Asn Arg Gly Glu Cys
225                 230

<210> SEQ ID NO 9
<211> LENGTH: 234
<212> TYPE: PRT
<213> ORGANISM: Artificial sequence
<220> FEATURE:
<223> OTHER INFORMATION: VLCL DR5 clone 5E11

<400> SEQUENCE: 9

Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
                20                  25                  30

Ser Pro Gly Glu Arg Ala Thr Leu Ser Cys Arg Ala Ser Gln Ser Val
                35                  40                  45

Ser Ser Ser Tyr Leu Ala Trp Tyr Gln Gln Lys Pro Gly Gln Ala Pro
                50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Gly Thr
                100                 105                 110

Thr His Pro Ile Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
                210                 215                 220

Val Thr Lys Ser Phe Asn Arg Gly Glu Cys
225                 230

<210> SEQ ID NO 10
<211> LENGTH: 214
<212> TYPE: PRT
<213> ORGANISM: Artificial sequence
<220> FEATURE:
<223> OTHER INFORMATION: VLCH1 FAP clone 28H1
```

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210

<210> SEQ ID NO 11
<211> LENGTH: 924
<212> TYPE: DNA
<213> ORGANISM: Artificial sequence
<220> FEATURE:
<223> OTHER INFORMATION: VHCH1-CMP-Flag DR5 clone 2A11

<400> SEQUENCE: 11

```
atgggatgga gctgtatcat cctcttcttg gtagcaacag ctaccggtgt gcattccgag      60
gtgcaattgt tggagtctgg gggaggcttg gtacagcctg gggggtccct gagactctcc     120
tgtgcagcct ccggattcac ctttagcagt tatgccatga gctgggtccg ccaggctcca     180
gggaagggc tggagtgggt ctcagctatt agtggtagtg gtggtagcac atactacgca     240
gactccgtga agggccggtt caccatctcc agagacaatt ccaagaacac gctgtatctg     300
cagatgaaca gcctgagagc cgaggacacg gccgtatatt actgtgcgcg tggtccgtac     360
ggtcgttacg ctgctctgga ctactggggc caaggaaccc tggtcaccgt ctcgagtgct     420
agcacaaagg gacctagcgt gttcccctg gccccagca gcaagtctac atctggcgga     480
acagccgccc tgggctgcct cgtgaaggac tactttcccg agcccgtgac cgtgtcctgg     540
aactctggcg ctctgacaag cggcgtgcac acctttccag ccgtgctgca gagcagcggc     600
ctgtactctc tgagcagcgt cgtgacagtg cccagcagct ctctgggcac ccagacctac     660
atctgcaacg tgaaccacaa gcccagcaac accaaggtgg acaagaaggt ggaacccaag     720
```

| | |
|---|---|
| agctgcgacg gcggagggggg atctggcggc ggaggatccg aagaagatcc ttgcgcctgc | 780 |
| gagagcctcg tgaaattcca ggccaaggtg aaggactgc tgcaggccct gacccggaaa | 840 |
| ctggaagccg tgtccaagcg gctggccatc ctggaaaaca ccgtggtggc cagcgactac | 900 |
| aaggacgacg acgacaagtc cgga | 924 |

<210> SEQ ID NO 12
<211> LENGTH: 915
<212> TYPE: DNA
<213> ORGANISM: Artificial sequence
<220> FEATURE:
<223> OTHER INFORMATION: VHCH1-CMP-Flag DR5 clone 5E11

<400> SEQUENCE: 12

| | |
|---|---|
| atgggatgga gctgtatcat cctcttcttg gtagcaacag ctaccggtgt gcattccgag | 60 |
| gtgcaattgt tggagtctgg gggaggcttg gtacagcctg gggggtccct gagactctcc | 120 |
| tgtgcagcct ccggattcac ctttagcagt tatgccatga gctgggtccg ccaggctcca | 180 |
| gggaaggggc tggagtgggt ctcagctatt agtggtagtg gtggtagcac atactacgca | 240 |
| gactccgtga agggccggtt caccatctcc agagacaatt ccaagaacac gctgtatctg | 300 |
| cagatgaaca gcctgagagc cgaggacacg gccgtatatt actgtgcgaa agggggtgagg | 360 |
| gtgtcttttg actactgggg ccaaggaacc ctggtcaccg tctcgagtgc tagcacaaag | 420 |
| ggacctagcg tgttcccct ggccccagc agcaagtcta catctggcgg aacagccgcc | 480 |
| ctgggctgcc tcgtgaagga ctactttccc gagcccgtga ccgtgtcctg gaactctggc | 540 |
| gctctgacaa gcgcgtgca cacctttcca gccgtgctgc agagcagcgg cctgtactct | 600 |
| ctgagcagcg tcgtgacagt gcccagcagc tctctgggca cccagaccta catctgcaac | 660 |
| gtgaaccaca gcccagcaa caccaaggtg gacaagaagg tggaacccaa gagctgcgac | 720 |
| ggcggagggg gatctggcgg cggaggatcc gaagaagatc cttgcgcctg cgagagcctc | 780 |
| gtgaaattcc aggccaaggt ggaaggactg ctgcaggccc tgacccggaa actggaagcc | 840 |
| gtgtccaagc ggctggccat cctggaaaac accgtggtgg ccagcgacta caaggacgac | 900 |
| gacgacaagt ccgga | 915 |

<210> SEQ ID NO 13
<211> LENGTH: 1584
<212> TYPE: DNA
<213> ORGANISM: Artificial sequence
<220> FEATURE:
<223> OTHER INFORMATION: 5E11_28H1 CrossFab VHCH1-CMP-VHCL

<400> SEQUENCE: 13

| | |
|---|---|
| gaggtgcaat gttggagtc tgggggaggc ttggtacagc ctggggggtc cctgagactc | 60 |
| tcctgtgcag cctccggatt cacctttagc agttatgcca tgagctgggt ccgccaggct | 120 |
| ccagggaagg gctggagtg gtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gaaagggggtg | 300 |
| agggtgtctt ttgactactg ggggccaagga accctggtca ccgtctcgag tgctagcaca | 360 |
| aagggaccta gcgtgttccc cctggccccc agcagcaagt ctacatctgg cggaacagcc | 420 |
| gccctgggct gcctcgtgaa ggactacttt cccgagcccg tgaccgtgtc ctggaactct | 480 |
| ggcgctctga caagcggcgt gcacaccttt ccagccgtgc tgcagagcag cggcctgtac | 540 |
| tctctgagca gcgtcgtgac agtgcccagc agctctctgg gcacccagac ctacatctgc | 600 |

```
aacgtgaacc acaagcccag caacaccaag gtggacaaga aggtggaacc caagagctgc     660
gacggcggag ggggatctgg cggcggagga tccgaagaag atccttgcgc ctgcgagagc     720
ctcgtgaaat ccaggccaa ggtggaagga ctgctgcagg ccctgacccg gaaactggaa      780
gccgtgtcca gcggctggc catcctggaa aacaccgtgg tggccagcga ctacaaggac      840
gacgacgaca gtccggagg cggcggaagc ggaggaggag gatccggagg agggggaagt      900
ggcggcggag gatctgaggt gcagctgctg gaatccggcg gaggcctggt gcagcctggc     960
ggatctctga gactgtcctg cgccgcctcc ggcttcacct tctcctccca cgccatgtcc    1020
tgggtccgac aggctcctgg caaaggcctg gaatgggtgt ccgccatctg gcctccggc    1080 gagcagtact acgccgactc tgtgaagggc cggttcacca tctcccggga caactccaag    1140
aacaccctgt acctgcagat gaactccctg cgggccgagg acaccgccgt gtactactgt    1200
gccaagggct ggctgggcaa cttcgactac tggggccagg gcaccctggt caccgtgtcc    1260
agcgctagcg tggccgctcc cagcgtgttc atcttcccac ccagcgacga gcagctgaag    1320
tccggcacag ccagcgtggt gtgcctgctg aacaacttct accccgcga ggccaaggtg    1380 cagtggaagg tggacaacgc cctgcagagc ggcaacagcc aggaatccgt gaccgagcag    1440
gacagcaagg actccaccta cagcctgagc agcaccctga ccctgagcaa ggccgactac    1500
gagaagcaca aggtgtacgc ctgcgaagtg acccaccagg gcctgtccag ccccgtgacc    1560
aagagcttca accggggcga gtgc                                            1584

<210> SEQ ID NO 14
<211> LENGTH: 1617
<212> TYPE: DNA
<213> ORGANISM: Artificial sequence
<220> FEATURE:
<223> OTHER INFORMATION: 5E11_28H1 scFv VHCH1-CMP-VHVL

<400> SEQUENCE: 14
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggggtg    300
agggtgtctt ttgactactg gggccaagga accctggtca ccgtctcgag tgctagcaca    360
aagggaccta gcgtgttccc cctggccccc agcagcaagt ctacatctgg cggaacagcc    420
gccctgggct gcctcgtgaa ggactacttt cccgagcccg tgaccgtgtc ctggaactct    480
ggcgctctga caagcggcgt gcacaccttt ccagccgtgc tgcagagcag cggcctgtac    540
tctctgagca gcgtcgtgac agtgcccagc agctctctgg gcacccagac ctacatctgc    600
aacgtgaacc acaagcccag caacaccaag gtggacaaga aggtggaacc caagagctgc    660
gacggcggag ggggatctgg cggcggagga tccgaggaag atccttgcgc ctgcgagagc    720
ctcgtgaagt ccaggccaa ggtggaagga ctgctgcagg ccctgacccg gaaactggaa     780
gccgtgtcca gcggctggc catcctggaa aacaccgtgg tgtccggagg cggggtagc      840 ggcggagggg gctctggcgg tggcgggtct ggaggcgggg gttcagaagt gcagctgctg    900
gaatctggcg gcggactggt gcagcctggc ggatctctga gactgagctg tgccgccagc    960
ggcttcacct ttagcagcca cgccatgagc tgggtgcgcc aggcccctgg aaagtgcctg   1020
```

| | |
|---|---|
| gaatgggtgt ccgccatctg ggccagcggc gagcagtact acgccgatag cgtgaagggc | 1080 |
| cggttcacca tcagccggga caacagcaag aacaccctgt acctgcagat gaacagcctg | 1140 |
| cgggccgagg acaccgccgt gtactattgt gccaagggct ggctgggcaa cttcgactat | 1200 |
| tggggccagg gcaccctcgt gaccgtgtct agcggagggg gcggaagtgg tgcgggggga | 1260 |
| agcggcgggg gtggcagcgg aggggcgga tctgaaattg tgctgaccca gagccctggc | 1320 |
| accctgagcc tgtctccagg cgaaagagcc acactgagct gcagagccag ccagagcgtg | 1380 |
| tccagaagct acctggcctg gtatcagcag aagcccggac aggcccccag actgctgatc | 1440 |
| atcggcgcct ctacaagagc caccggcatc cccgatagat cagcggctc tggcagcggc | 1500 |
| accgacttca ccctgaccat cagcagactg gaacccgagg actttgccgt gtattactgc | 1560 |
| cagcagggcc aagtgatccc ccccacctt ggctgtggca caaggtgga aatcaaa | 1617 |

<210> SEQ ID NO 15
<211> LENGTH: 867
<212> TYPE: DNA
<213> ORGANISM: Artificial sequence
<220> FEATURE:
<223> OTHER INFORMATION: CMP-28H1 CrossFab

<400> SEQUENCE: 15

| | |
|---|---|
| ggatccgagg aagatccttg cgcctgcgag agcctcgtga agttccaggc caaggtggaa | 60 |
| ggactgctgc aggccctgac ccggaaactg aagccgtgt ccaagcggct ggccatcctg | 120 |
| gaaaacaccg tggtgtccgg aggcggcgga agcggaggag gaggatccgg aggaggggga | 180 |
| agtggcggcg gaggatctga ggtgcagctg ctggaatccg gcgaggcct ggtgcagcct | 240 |
| ggcggatctc tgagactgtc ctgcgccgcc tccggcttca ccttctcctc ccacgccatg | 300 |
| tcctgggtcc gacaggctcc tggcaaaggc ctggaatggg tgtccgccat ctgggcctcc | 360 |
| ggcgagcagt actacgccga ctctgtgaag ggccggttca ccatctcccg ggacaactcc | 420 |
| aagaacaccc tgtacctgca gatgaactcc ctgcgggccg aggacaccgc cgtgtactac | 480 |
| tgtgccaagg gctggctggg caacttcgac tactggggcc agggcaccct ggtcaccgtg | 540 |
| tccagcgcta gcgtggccgc tcccagcgtg ttcatcttcc cacccagcga cgagcagctg | 600 |
| aagtccggca cagccagcgt ggtgtgcctg ctgaacaact ctaccccg cgaggccaag | 660 |
| gtgcagtgga aggtggacaa cgccctgcag agcggcaaca gccaggaatc cgtgaccgag | 720 |
| caggacagca aggactccac ctacagcctg agcagcaccc tgaccctgag caaggccgac | 780 |
| tacgagaagc acaaggtgta cgcctgcgaa gtgacccacc agggcctgtc cagcccgtg | 840 |
| accaagagct caaccggggg cgagtgc | 867 |

<210> SEQ ID NO 16
<211> LENGTH: 699
<212> TYPE: DNA
<213> ORGANISM: Artificial sequence
<220> FEATURE:
<223> OTHER INFORMATION: VLCL DR5 clone 2A11

<400> SEQUENCE: 16

| | |
|---|---|
| atgggatgga gctgtatcat cctcttcttg gtagcaacag ctaccggtgt gcattccgac | 60 |
| atccagatga cccagagccc cagcagcctg agcgccagcg tgggcgacag agtgaccatc | 120 |
| acctgcagcg ccagccaggg catccggaac tacctgaact ggtatcagca gaagcccggc | 180 |
| aaggcccca agctgctgat ctactacacc agcagcctgc acagcggcgt gcctagccgg | 240 |
| tttagcggca gcggctccgg caccgacttc accctgacca ttagctccct gcagcccgag | 300 |

```
gacttcgcca cctactactg ccagcagtac agcaagctgc cctggacctt cggccaggga      360
acaaaggtgg agatcaagcg tacggtggct gcaccatctg tcttcatctt cccgccatct      420
gatgagcagt tgaaatctgg aactgcctct gttgtgtgcc tgctgaataa cttctatccc      480
agagaggcca agtacagtg gaaggtggat aacgccctcc aatcgggtaa ctcccaggag       540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgt                             699
```

```
<210> SEQ ID NO 17
<211> LENGTH: 702
<212> TYPE: DNA
<213> ORGANISM: Artificial sequence
<220> FEATURE:
<223> OTHER INFORMATION: VLCL DR5 clone 5E11

<400> SEQUENCE: 17
atgggatgga gctgtatcat cctcttcttg gtagcaacag ctaccggtgt gcattccgaa      60
atcgtgttaa cgcagtctcc aggcaccctg tctttgtctc caggggaaag agccaccctc     120
tcttgcaggg ccagtcagag tgttagcagc agctacttag cctggtacca gcagaaacct    180
ggccaggctc ccaggctcct catctatgga gcatccagca gggccactgg catcccagac    240
aggttcagtg gcagtggatc cgggacagac ttcactctca ccatcagcag actggagcct    300
gaagattttg cagtgtatta ctgtcagcag ggtactactc atcccattac gttcggccag    360
gggaccaaag tggaaatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gt                        702
```

```
<210> SEQ ID NO 18
<211> LENGTH: 642
<212> TYPE: DNA
<213> ORGANISM: Artificial sequence
<220> FEATURE:
<223> OTHER INFORMATION: VLCH1FAP clone 28H1

<400> SEQUENCE: 18
gagatcgtgc tgacccagtc tcccggcacc ctgagcctga gcctggcga gagagccacc       60 ctgagctgca gagccagcca gagcgtgagc cggagctacc tggcctggta tcagcagaag     120
cccggccagg cccccagact gctgatcatc ggcgccagca cccgggccac cggcatcccc     180
gatagattca gcggcagcgg ctccggcacc gacttcaccc tgaccatcag ccggctggaa    240
cccgaggact tcgccgtgta ctactgccag cagggccagg tgatccccc cacccttcggc    300 cagggcacca aggtggaaat caagagctcc gctagcacca agggcccctc cgtgtttcct    360
ctggccccca gcagcaagag cacctctggc ggaacagccg ccctgggctg cctggtgaaa    420
gactacttcc ccgagcccgt gaccgtgtcc tggaactctg gcgccctgac cagcggcgtg    480
cacacctttc cagccgtgct gcagagcagc ggcctgtact ccctgagcag cgtggtgaca    540
gtgccctcca gcagcctggg cacccagacc tacatctgca acgtgaacca caagcccagc    600
```
aacaccaaag tggacaagaa ggtggaaccc aagagctgcg ac                               642

<210> SEQ ID NO 19
<211> LENGTH: 561
<212> TYPE: PRT
<213> ORGANISM: Artificial sequence
<220> FEATURE:
<223> OTHER INFORMATION: Anti-Digoxigenin(Fab-HC)-CMP-anti-
      CEA(scFv)Digoxigenin

<400> SEQUENCE: 19

```
Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Ala Met Ser Trp Ile Arg Gln Ala Pro Gly Lys Gly Leu
    50                  55                  60

Glu Trp Val Ser Ser Ile Asn Ile Gly Ala Thr Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Pro Gly Ser Pro Tyr Glu Tyr Asp Lys Ala Tyr
        115                 120                 125

Tyr Ser Met Ala Tyr Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Gly Gly Gly Gly Ser
                245                 250                 255

Gly Gly Gly Gly Ser Glu Glu Asp Pro Cys Ala Cys Glu Ser Leu Val
            260                 265                 270

Lys Phe Gln Ala Lys Val Glu Gly Leu Leu Gln Ala Leu Thr Arg Lys
        275                 280                 285

Leu Glu Ala Val Ser Lys Arg Leu Ala Ile Leu Glu Asn Thr Val Val
    290                 295                 300

Gly Gly Gly Gly Ser Gly Gly Gly Ser Gln Val Lys Leu Glu Gln
305                 310                 315                 320

Ser Gly Ala Glu Val Val Lys Pro Gly Ala Ser Val Lys Leu Ser Cys
                325                 330                 335

Lys Ala Ser Gly Phe Asn Ile Lys Asp Ser Tyr Met His Trp Leu Arg
            340                 345                 350
```

Gln Gly Pro Gly Gln Cys Leu Glu Trp Ile Gly Trp Ile Asp Pro Glu
            355                 360                 365

Asn Gly Asp Thr Glu Tyr Ala Pro Lys Phe Gln Gly Lys Ala Thr Phe
        370                 375                 380

Thr Thr Asp Thr Ser Ala Asn Thr Ala Tyr Leu Gly Leu Ser Ser Leu
385                 390                 395                 400

Arg Pro Glu Asp Thr Ala Val Tyr Tyr Cys Asn Glu Gly Thr Pro Thr
                405                 410                 415

Gly Pro Tyr Tyr Phe Asp Tyr Trp Gly Gln Gly Thr Leu Val Thr Val
            420                 425                 430

Ser Ser Gly Gly Gly Gly Ser Gly Gly Gly Ser Gly Gly Gly Gly
            435                 440                 445

Ser Gly Gly Gly Gly Ser Glu Asn Val Leu Thr Gln Ser Pro Ser Ser
    450                 455                 460

Met Ser Val Ser Val Gly Asp Arg Val Thr Ile Ala Cys Ser Ala Ser
465                 470                 475                 480

Ser Ser Val Pro Tyr Met His Trp Leu Gln Gln Lys Pro Gly Lys Ser
                485                 490                 495

Pro Lys Leu Leu Ile Tyr Ser Thr Ser Asn Leu Ala Ser Gly Val Pro
            500                 505                 510

Ser Arg Phe Ser Gly Ser Gly Ser Gly Thr Asp Tyr Ser Leu Thr Ile
            515                 520                 525

Ser Ser Val Gln Pro Glu Asp Ala Ala Thr Tyr Tyr Cys Gln Gln Arg
    530                 535                 540

Ser Ser Tyr Pro Leu Thr Phe Gly Cys Gly Thr Lys Leu Glu Ile Lys
545                 550                 555                 560

Arg

<210> SEQ ID NO 20
<211> LENGTH: 234
<212> TYPE: PRT
<213> ORGANISM: Artificial sequence
<220> FEATURE:
<223> OTHER INFORMATION: Anti-Digoxigenin(Fab-LC)

<400> SEQUENCE: 20

Met Glu Ala Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Lys Asn Tyr Leu Asn Trp Tyr Gln Gln Lys Pro Gly Lys Ala Pro
    50                  55                  60

Lys Leu Leu Ile Tyr Tyr Ser Thr Leu Leu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Ile
            100                 105                 110

Thr Leu Pro Pro Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr

```
                    145                 150                 155                 160
Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 21
<211> LENGTH: 1686
<212> TYPE: DNA
<213> ORGANISM: Artificial sequence
<220> FEATURE:
<223> OTHER INFORMATION: Anti-Digoxigenin(Fab-HC)-CMP-anti-CEA(scFv)

<400> SEQUENCE: 21
atgggctggt cctgcatcat cctgtttctg gtggccaccg ctaccggcgt ccatagccag      60
gtgcagctgg tggaaagcgg cggaggcctg gtgaaaccgg aggctctctc tgagactgtct    120
tgcgctgcga gcggctttac ctttagcgat tatgcgatga gctggattcg ccaggcgccg    180
ggcaaaggcc tggaatgggt gagcagcatt aacattggcg cgacctatat ttattatgcg    240
gatagcgtga aaggccgctt taccattagc cgcgataacg cgaaaaacag cctgtatctg    300
cagatgaata gcctcagagc ggaagataca gcggtgtatt attgcgcgcg cccgggcagc    360
ccgtatgaat atgataaagc gtattatagc atggcgtatt ggggccaggg caccaccgtg    420
acagtgagca gcgcgtcgac taagggccct tcagttttc cactcgcccc cagtagcaag    480
tccacatctg ggggtaccgc tgccctgggc tgccttgtga agactatttt ccctgaacca    540
gtcactgtgt catggaatag cggagccctg acctccggtg tacacacatt ccccgctgtg    600
ttgcagtcta gtggcctgta cagcctctcc tctgttgtga ccgtcccttc aagctccctg    660
gggacacaga cctatatctg taacgtgaat cataagccat ctaacactaa ggtagataaa    720
aaagtggagc caagagttg cgacaaaaca cacggaggtg gtggatctgg cggaggtggc    780
agtgaggaag acccctgcgc ctgtgagagc ctggtgaagt ccaggctaa gtcgagggc     840
ctcctgcagg cacttaccag gaagctggaa gccgtgtcca agagactcgc tatcctggag    900
aacacagtcg tgggcggagg cggttcaggg ggaggcggta gccaagtgaa gctggagcag    960
agcggcgccg aagtcgtgaa acccggggct tccgtcaagc tctcttgcaa ggcatcagga   1020
ttcaacatca agacagcta catgcactgg ctgaggcagg ccctggtca gtgccttgag    1080
tggattggct ggatcgatcc agagaatggc gacaccgaat atgcccccaa gtttcaagga   1140
aaggctacat tcaccactga tacatccgca aacaccgcct acctgggtct ctcaagtctg   1200
cgccctgagg acactgctgt gtattactgt aatgagggca cccccaacagg gccctactat   1260
tttgactact ggggacaggg caccttggtt acagtgagct ccgggggagg cggttccggg   1320
ggcggaggtt ctgggggcgg aggttctggc ggggaggc cagagaacgt gctgacccag   1380
agcccctcct ctatgtcagt cagcgtgggc gacagggtca caatcgcctg ctccgcttct   1440
agtagcgtgc cttacatgca ctggctccag cagaagccag gaaatcccc caagctgctt   1500
atttattcta cctcaaatct ggcaagcgga gttcctagca gattctctgg cagtggtagc   1560
```

-continued

```
gggactgatt actccctcac aatctcaagt gtgcagccag aagacgccgc tacctattac    1620
tgtcaacagc gcagctccta cccctgact tttggctgtg gcaccaagtt ggagattaaa    1680
cggtga                                                               1686

<210> SEQ ID NO 22
<211> LENGTH: 705
<212> TYPE: DNA
<213> ORGANISM: Artificial sequence
<220> FEATURE:
<223> OTHER INFORMATION: Anti-Digoxigenin(Fab-LC)

<400> SEQUENCE: 22
atggaagccc cagctcagct tctcttcctc ctgctactct ggctcccaga taccaccgga      60
gatattcaga tgacccagag cccgagcagc ctgagcgcga gcgtgggcga tcgcgtgacc     120
attacctgcc gcgcgagcca ggatattaaa aactatctga ctggtatca gcagaaaccg      180 ggcaaagcgc cgaaactgct gatttattat agcagcaccc tgctgagcgg cgtgccgagc     240
cgctttagcg gcagcggcag cggcaccgat tttaccctga ccattagcag cctgcagccg     300
gaagattttg cgacctatta ttgccagcag agcattaccc tgccgccgac ctttggcggc     360
ggcaccaaag tggaaattaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttag                    705
```

TRIMERIC ANTIGEN BINDING MOLECULES

CROSS REFERENCE TO RELATED APPLICATIONS

This application is a continuation of International Application No. PCT/EP2014/059030 having an international filing date of May 5, 2014, the entire contents of which are incorporated herein by reference, and which claims benefit under 35 U.S.C. § 119 to European Patent Application No. 13166793.3, filed May 7, 2013.

SEQUENCE LISTING

This application hereby incorporates by reference the material of the electronic Sequence Listing filed concurrently herewith. The material in the electronic Sequence Listing is submitted as a text (.txt) file entitled "P31450_US_Sequence_listing.txt" created on Apr. 14, 2014 which has a file size of 47.4 KB, and is herein incorporated by reference in its entirety.

FIELD OF THE INVENTION

The present invention pertains to a trimeric antigen binding molecule comprising three fusion polypeptides, each comprising at least one antigen binding moiety fused to a trimerization domain derived from human cartilage matrix protein, compositions thereof and its use as a medicament.

BACKGROUND

Several approaches have been described to generate artificial oligomers with defined stoichiometries of recombinant antibodies or other proteins. This is desired, either because the binding affinity of a given protein to its target can be increased by multimerization, or because a certain biological effect can only be obtained with a certain oligomerization grade of the active compound (Crothers, D. M. & Metzger, H. (1972). The influence of polyvalency on the binding properties of antibodies. Immunochemistry, 9, 341-357). Another, newer review describes the effects of valency not only on functional affinity, but also on pharmacokinetics due to optimized molecular weight (Deyev S. M. & Lebedenko E. N. 2008, BioEssays 30:904-918).

Shu and coworkers have generated a variant of the GCN4 leucine zipper, that naturally is a dimer but in an engineered version forms a trimeric coil coil structure and used it to analyze the nature of trimeric assembly of the HIV-1 protein gp41 (Chemistry. 1999 Apr. 27; 38(17):5378-85).

Wyzgol and coworkers describe the usage of a trimerization domain from the chicken protein tenascin (amino acids 110-139, of UniProt entry: P10039. J Immunol 2009; 183: 1851-1861), for the artificial trimerization of ligands of the TNF receptor superfamily. Biological activity could be strongly enhanced for some of their examples.

Secreted hemagglutinins with or without a carboxy-terminal trimerization domain based on the natural trimerization domain of T4 phage fibritin were expressed by Krammer and coworkers (PLOS ONE 2012, Volume 7, Issue 8, e43603). They demonstrated that the antigen was kept by this trimerization in a native like structure and was recognized by some epitope specific antibodies.

The first examples of dimeric or trimeric antibodies were the diabodies or triabodies (reviewed by Kortt and coworkers in Biomol Eng. 2001 Oct. 15; 18(3):95-108.). Those assemblies are essentially composed of scFv fragments where the interdomain linker is shortened such that the VH domain from one polypeptide cannot form a functional Fv with the VL domain from the same polypeptide, but form functional Fvs in an interchain manner.

An early review by Pluckthun and colleagues summarizes different approaches to generate dimeric or tetrameric scFv antibody fragment fusions (Immunotechnology 3 (1997) 83-105). Here the authors use the oligomerization domains that are either coiled-coil leucine zipper domains or are derived from the tetramerization domain of the human p53 tumor suppressor protein. Also a quantitative estimation is given on the enhancement of binding strength by multimerization of a given binding domain. For the purpose of generating a bivalent display of antibody fragments on a filamentous phage Lee and colleagues used a similar homodimerizing leucine zipper. Bivalent display was first achieved by the insertion of a dimerization domain, consisting of an IgG1 hinge region and a homodimerizing GCN4 leucine zipper, between a Fab and the C-terminal domain of the M13 gene-3 minor coat protein. Covalent linkage of the two zipper domains was obtained via the disulfide bonds coming from the hinge region, and display it on a phage for the screening of antibody libraries (J Immunol Methods. 2004 January; 284(1-2):119-32).

Cuesta and coworkers describe the usage of the Trimerization domains of either collagen XV or collagen XVIII for the generation of a trimeric scFv molecule, named trimerbody (2012, mAbs 4:2, 226-232). The trimerized constructs showed an almost 100-fold increase of the functional affinity compared to a monovalent scFv of the same specificity. Both trimerization domains form non-covalent trimers (Boudko et al.; J. Mol. Biol. (2009) 392, 787-802, and Wirz et al.; Matrix Biology 30 (2011) 9-15).

Binding of a ligand or antibody in a trimeric form to a certain receptor can have significant advantages over binding of monomeric or dimeric modules (like an IgG). Especially, binding to receptors of the TNFR family that induce apoptosis in the target cell after induced trimerization could generate a therapeutic benefit. Allen and coworkers generated a binder to Death receptor 4 based on a tetranectin C-type lectin domain (Mol Cancer Ther 2012; 11:2087-2095). This binding domain was trimerized via the coiled-coil motif obtained from the same tetranectin protein. This protein forms non-covalent homo-trimers. One of those trimeric molecules induced apoptosis in DR4 expressing cells, similar to the natural trimeric TRAIL ligand. This novel class of molecules was named atrimers by the authors (Mol Cancer Ther 2012; 11:2087-2095).

Fab fragments of an anti-ICAM-1 antibody were assembled into dimeric, trimeric or tetrameric format using the multimerization domain derived from either of the human transcription factors, ATFα or CREBPa (Charles et al.; Journal of Immunological Methods 284 (2004) 119-132). The oligomerization domains used here all share a coiled-coil motif, and assemble without the formation of covalent oligomers. These proteins successfully blocked rhinovirus infection in vitro, with the efficiency increasing from monomer to dimer, trimer, and tetramer.

So called "peptabodies" were generated by Terskikh and colleagues (Proc Natl Acad Sci USA. 1997 Mar. 4; 94(5): 1663-8). A short peptide ligand was fused via a semi-rigid hinge region with the coiled-coil assembly domain of the cartilage oligomeric matrix protein (COMP), resulting in a pentameric multivalent binding molecule.

Heptamerization of binding domains from protein Z were generated via the heptamerization domain of the Archaeal RNA binding protein Sm1 through a flexible hinge peptide (Kim et al.; PLoS One. 2012; 7(8):e43077). Surface plasmon resonance (SPR) analysis showed that both heptameric anti-EGFR and anti-HER2 binders have a significantly enhanced binding strength to their target receptors with a nearly 100 to 1000 fold increase relative to the monomeric ligands.

Another approach to generate polyvalency was described by Li et al., and is named "chemically self-assembled antibody nanorings (CSANs)" (J. AM. CHEM. SOC. 2010, 132, 17247-17257). The authors designed it such that each nanoring subunit is composed of a number of artificial dimers of E. coli DHFR that assemble to the ring-like structures when a dimeric version of methotrexate (named: MTX2-C9) is added.

Bispecific antibodies present unique opportunities in terms of new applications for engineered antibodies. However, designing ideal bispecific antibodies remains a challenge.

Fick and coworkers give an overview on the generation of different bispecific reagents that comprise a scFv fragment fused to the trimerization domain of tenascin which is fused to a ligand of the TNF family (Patrick Chames (ed.), Antibody Engineering: Methods and Protocols, Second Edition, Methods in Molecular Biology, vol. 907, 597-609). Trimerization is stabilized by naturally occurring interchain disulfide bonds. Those molecules are useful for targeting approaches where the active, trimeric apoptosis inducer is delivered to a tumor cell via the anti-tumor binding capacity of the scFv fragment.

Stone and coworkers describe a novel bispecific antibody model in which five single domain antibodies (sdAbs) are fused via a linker sequence to the N-terminus of the verotoxin B (VTB) subunit, a pentamerization domain, and five sdAbs are fused via a linker sequence to the VTB C-terminus (Journal of Immunological Methods, (2007) 318 (1-2) pp. 88-94.). Several of such decavalent bispecific molecules, termed decabodies, were constructed and characterized. Albeit an interesting concept, the physico-chemical properties of those molecules are still to be optimized.

Kashentseva and coworkers use the fibritin domain of phage T4 to generate a bispecific, trimeric fusion protein that should redirect Adenoviruses to a tumor cell (Cancer Res Jan. 15, 2002 62; 609).

Provided herein are novel trimeric antigen binding molecules comprising a trimerisation domain derived from human cartilage matrix protein. Since the trimerization domain is derived from a protein of human origin the trimeric antigen binding molecule has a lower probability of immunogenicity compared to molecules with a polymerization domain of non-human origin. In addition, the trimerization domain derived from human cartilage matrix protein trimerizes into a coiled-coil structure through naturally occurring disulfide bonds which leads to a stable trimeric antigen binding molecule that can be used both in a monospecific and in a bispecific format.

SUMMARY OF THE INVENTION

In a first aspect the present invention provides a trimeric antigen binding molecule comprising three fusion polypeptides, each comprising at least one antigen binding moiety fused to a trimerization domain derived from human cartilage matrix protein (CMP, SEQ ID NO:1), wherein said trimerization domain is capable of mediating stable association of the trimeric antigen binding molecule.

In one embodiment the trimerization domain of the trimeric antigen binding molecule comprises a sequence having at least 95% identity to SEQ ID NO: 2. In one embodiment the trimerization domain of the trimeric antigen binding molecule comprises the sequence of SEQ ID NO: 2.

In one embodiment the three fusion polypeptides of the trimeric antigen binding molecule are linked by disulfide bonds. In one embodiment the antigen binding moiety is an antibody or an antibody fragment. In one embodiment the antigen binding moiety is an antibody fragment, selected from the group consisting of a Fab molecule, a crossover Fab molecule, a single chain Fab molecule, an Fv molecule, a scFv molecule and a single domain antibody.

In one embodiment the three fusion polypeptides of the trimeric antigen binding molecule each comprise one antigen binding moiety. In one embodiment said antigen binding moiety is a Fab molecule. In one embodiment said Fab molecule is fused at the C-terminal amino acid of the Fab heavy chain to the N-terminal amino acid of said trimerization domain, optionally through a peptide linker. In one embodiment the antigen binding moiety is capable of specific binding to a cell surface antigen. In one embodiment said cell surface antigen is a tumor cell antigen.

In one embodiment the three fusion polypeptides of the trimeric antigen binding molecule each comprise two antigen binding moieties. In one such embodiment the first antigen binding moiety is fused to the N-terminal amino acid of said trimerization domain, optionally through a peptide linker and the second antigen binding moiety is fused to the C-terminal amino acid of said trimerization domain, optionally through a peptide linker.

In one embodiment said first antigen binding moiety is a Fab molecule and said second antigen binding moiety is a scFv molecule or a crossover Fab molecule.

In one embodiment said first antigen binding moiety is a Fab molecule which is fused at the N-terminal amino acid of the Fab heavy chain to the C-terminal amino acid of said trimerization domain, optionally through a peptide linker.

In one embodiment said first or second antigen binding moiety is capable of specific binding to a cell surface antigen.

In one embodiment said first or second antigen binding moiety is capable of specific binding to a hapten.

In one embodiment a trimeric antigen binding molecule is provided, essentially consisting of three fusion polypeptides each consisting of an antigen binding moiety fused to said trimerization domain, optionally through a peptide linker.

In one embodiment a trimeric antigen binding molecule is provided, essentially consisting of three fusion polypeptides each consisting of a first and a second antigen binding moiety fused to said trimerization domain, optionally through a peptide linker.

In one embodiment said three fusion polypeptides of any of the above embodiments are identical.

In one embodiment a fusion polypeptide is provided, comprising an antigen binding moiety fused to a trimerization domain derived from human cartilage matrix protein (CMP, SEQ ID NO: 1), wherein said trimerization domain is capable of mediating stable association of said fusion polypeptide with two further such fusion polypeptides According to another aspect of the invention there is provided an isolated polynucleotide encoding a trimeric antigen binding molecule of the invention or a fragment thereof. The invention also encompasses polypeptides encoded by the polynucleotides of the invention. The invention further provides an expression vector comprising the isolated polynucleotide of the invention, and a host cell comprising the isolated polynucleotide or the expression vector of the invention. In some embodiments the host cell is a eukaryotic cell, particularly a mammalian cell.

In another aspect is provided a method of producing the trimeric antigen binding molecule of the invention, comprising the steps of a) culturing the host cell of the invention under conditions suitable for the expression of the trimeric antigen binding molecule and b) recovering the trimeric antigen binding molecule. The invention also encompasses a trimeric antigen binding molecule produced by the method of the invention.

The invention further provides a pharmaceutical composition comprising the trimeric antigen binding molecule of the invention and a pharmaceutically acceptable carrier.

Also encompassed by the invention are methods of using the trimeric antigen binding molecule and pharmaceutical composition of the invention. In one aspect the invention provides a trimeric antigen binding molecule or a pharmaceutical composition of the invention for use as a medicament. In one aspect is provided a trimeric antigen binding molecule or a pharmaceutical composition according to the invention for use in the treatment of a disease in an individual in need thereof. In a specific embodiment the disease is cancer.

Also provided is the use of a trimeric antigen binding molecule of the invention for the manufacture of a medicament for the treatment of a disease in an individual in need thereof; as well as a method of treating a disease in an individual, comprising administering to said individual a therapeutically effective amount of a composition comprising the trimeric antigen binding molecule according to the invention in a pharmaceutically acceptable form. In a specific embodiment the disease is cancer. In any of the above embodiments the individual preferably is a mammal, particularly a human.

BRIEF DESCRIPTION OF THE DRAWINGS

FIG. 2A) Trimerized huCMP anti-DR5 (5E11) Fab, FIG. 2B) Trimerized huCMP anti-DR5 (2A11) Fab. 1: molecular weight marker; 2: non-reduced samples; 3: reduced samples.

DETAILED DESCRIPTION OF THE INVENTION

Definitions

Figure 1:
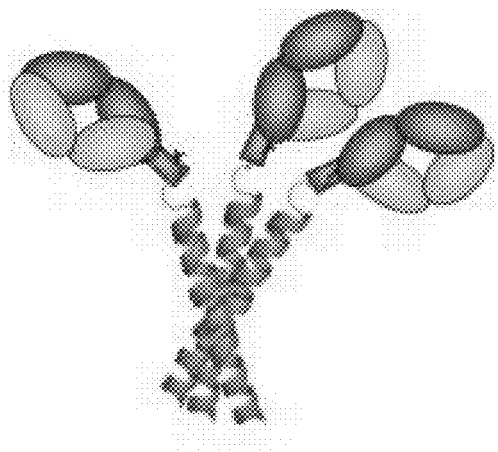
FIG. 1A: Schematic representation of trimeric monospecific antigen binding molecules, as exemplified by Fab arms bound to the CMP peptide.
FIG. 1B: Schematic representation of bispecific, hexavalent antigen binding molecule, as exemplified by fusing a Fab fragment in the CrossMab format to the Fab-CMP fusion.
Figure 1:
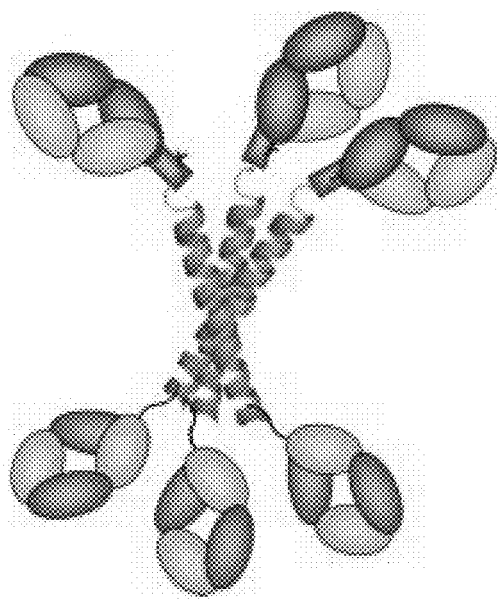

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The terms "CMP" or "cartilage matrix protein" refer to a protein also known as matrilin-1. MATN1 Synonyms: CMP, CRTM as described e.g. in Uniprot entry P21941.

The terms "CMP trimerization domain" or "trimerization domain derived from human cartilage matrix protein (CMP)" are used interchangeably therein and refer to a polypeptide structure capable of associating with two similar or identical polypeptides to form a stable trimer. The trimerisation is mediated through ionic bonds and other non-covalent bonds formed between adjacent charged amino acids of the polypeptide chains. The CMP trimerization domain has been been described e.g. in Beck et al, J. Mol. Biol. (1996) 256, 909-923. The CMP trimerization domain useful therein has been derived from human cartilage protein (SEQ ID No. 1) and in one embodiment comprises a sequence having at least 95% identity and most preferably at least 98% identity to SEQ ID NO 2. In one embodiment said trimerization domain comprises the sequence of SEQ ID NO. 2.

The term "monospecific" antibody as used herein denotes an antibody that has one or more binding sites each of which bind to the same epitope of the same antigen. The trimeric antigen binding molecule of the invention generally is monospecific, but may also be bispecific.

The term "bispecific" means that the antigen binding molecule is able to specifically bind to at least two distinct antigenic determinants. Typically, a bispecific antigen binding molecule comprises two antigen binding sites, each of which is specific for a different antigenic determinant.

In certain embodiments the bispecific antigen binding molecule is capable of simultaneously binding two antigenic determinants, particularly two antigenic determinants expressed on two distinct cells. The trimeric antigen binding molecules of the invention can be bispecific.

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The trimeric antigen binding molecules according to the invention are at least "trivalent" and may be "hexavalent".

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment an antigen binding moiety is able to activate signaling through its target antigen. In one embodiment, an antigen binding moiety is able to direct the entity to which it is attached (e.g. a second antigen binding moiety) to a target site, for example to a specific type of tumor cell or tumor stroma bearing the antigenic determinant. Antigen binding moieties include antibodies and fragments thereof as further defined herein. In addition, antigen binding moieties include binding domains which are based on designed repeat proteins or designed repeat domains (see e.g. WO 2002/020565).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

A "target cell antigen" as used herein refers to an antigenic determinant presented on the surface of a target cell, for example a cell in a tumor such as a cancer cell or a cell of the tumor stroma.

As used herein, the terms "first" and "second" with respect to antigen binding moieties etc., are used for convenience of distinguishing when there is more than one of each type of moiety. Use of these terms is not intended to confer a specific order or orientation of the trimeric antigen binding molecule unless explicitly so stated.

A "Fab molecule" or "Fab fragment" refers to a protein consisting of the VH and CH1 domain of the heavy chain (the "Fab heavy chain") and the VL and CL domain of the light chain (the "Fab light chain") of an immunoglobulin.

By "fused" or "connected" is meant that the components (e.g. a Fab molecule and an CMP trimerisation domain) are linked by peptide bonds, either directly or via one or more peptide linkers.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), (IgE), γ (IgG), or µ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia |
|---|---|---|
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table A is according to the numbering conventions set forth by Kabat et al. (see below).

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., increased stability of the trimeric antigen binding molecule. Amino acid sequence deletions and insertions include amino- and/or carboxyterminal deletions and insertions of amino acids. Particular amino acid mutations are amino acid substitutions. For the purpose of altering e.g. the stability of the trimeric antigen binding molecule, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

A "fusion polypeptide" as used herein refers to a polypeptide composed of at least one antigen binding moiety fused to a CMP trimerization domain. The fusion may occur by directly linking the N or C-terminal amino acid of the antigen binding moiety via a peptide bond to the C- or N-terminal amino acid of the CMP trimerization domain. In other embodiments the fusion may be achieved through a peptide linker.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the trimeric binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The objective of the present invention is to provide a novel trimeric antigen binding molecule comprising at least three antigen binding moieties.

The present invention pertains to a trimeric antigen binding molecule comprising three fusion polypeptides, each comprising at least one antigen binding moiety fused to a trimerization domain derived from human cartilage matrix protein (CMP, SEQ ID NO: 1), wherein said trimerization domain is capable of mediating stable association of the trimeric antigen binding molecule. The three fusion polypeptides bind to each other through ionic and other non-covalent bonds and thus form a trimeric molecule with at least three antigen binding moeities. Upon trimerisation, the fusion polypeptides form a stable coiled-coil structure, which provides the trimeric antigen binding molecule with stability.

In one embodiment of the invention the three adjacent fusion polypeptides associate to a trimer via interchain disulfide bonds between the trimerization domains. In the context of the present application the term "interchain disulfide bond" means that two fusion polypeptides are each connected through a disulfide bond formed between two cysteine residues in the amino acid sequence of the fusion polypeptide. Hence the three fusion polypeptides of the trimeric antigen binding molecule, form three disulfide bonds, each bond connecting two trimerization domains. Such interchain disulfide bonds generally occur naturally in the trimerization domain derived from human cartilage matrix protein, or they may be introduced alternatively or additionally to the trimeric binding molecule The additional disulfide bonds may be created by adding a cysteine at the N-terminal and/or C-terminal end of the amino acid sequences of the trimerization domain derived from human cartilage matrix protein, preferably to the N-terminal end. The additional disulfide bonds may also be introduced by substituting one or more of the amino acid residues in the trimerization domain with cysteine. The additional disulfide bonds may lead to an increased stability of the trimeric binding molecule.

The trimerization domain derived from human cartilage matrix protein (CMP) comprises at least a part of SEQ ID NO.: 1. In one embodiment the trimerization domain comprises a sequence having at least 95% identity and most preferably at least 98% identity to SEQ ID NO.: 2. In one embodiment said trimerization domain comprises the sequence of SEQ ID NO.: 2. The trimerization domain derived from human cartilage matrix protein (CMP) is therein further also referred to as "CMP trimerization domain".

In one embodiment of the invention the CMP trimerization domain comprises amino acids 454 to 496 of human CMP from Uniprot entry P21941. In another embodiment the CMP trimerization domain is derived from the cartilage matrix protein of the group selected from *Callithrix jacchus* (ref: XP_002750612.1), *Macaca mulatta* (ref: XP_001094970.1) and *Mus musculus* (Gene ID: 17180 Matn1).

In one embodiment the fusion polypeptides comprise each one antigen binding moiety fused to the CMP trimerization domain. Trimerization of the three fusion polypeptides results in assembly into a trimeric antigen binding molecule with three antigen binding moeities. The trimeric antigen binding molecule is hence a trivalent antigen binding molecule. In one embodiment the three antigen binding moieties are each specific for the same antigen, i.e. the trimeric antigen binding molecule is monospecific and trivalent.

Since there are three antigen binding moieties in each trimeric antigen binding molecules, the synergistic affinities of each antigen binding moiety to its target are increased.

Therefore the trimeric antigen binding molecules bind to the antigen with a higher avidity compared to a conventional bivalent IgG based antibody. Hence the trimeric binding molecule will be binding effectively at lower concentrations compared to conventional IgG-based antibodies. This allows for the use of a wide variety of antigen binding moieties, including antigen binding moieties with low affinities to the antigen. In addition, multimeric binding of the antigen binding moieties to its target can also result in enhanced signaling. Conversion of recombinant antibodies into multivalent format potentially optimizes biodistribution by decreasing dissociation rates from cell-surfaces.

Small-sized antibody fragments, for example, scFvs of ~25 kDa size, are not optimal for applications where a significant serum half-life is required, since they show relatively fast renal clearance. The half-life time for the clearance of a protein molecule correlates with its size; the threshold for glomerular filtration is estimated to be 60-65 kDa (Reviewed in: Trejtnar et al.; 2002, Q J Nucl Med 46:181-194). Oligomerization of such small domains can therefore increase the mass above a critical threshold for glomerular filtration and therefore increase serum half-life.

In one embodiment the antigen binding moieties of the trimeric antigen binding molecule are capable of specific binding to a cell surface antigen. In one embodiment, said cell surface antigen is a tumor cell antigen.

In one embodiment the fusion polypeptides comprise each two antigen binding moieties fused to the CMP trimerization domain. In one embodiment the trimeric antigen binding molecule comprises three fusion polypeptides wherein a first antigen binding moiety is fused to the N-terminus of the CMP trimerisation domain, and a second antigen binding moiety is fused to the C-terminus of the CMP trimerisation domain. Trimerization of the three fusion polypeptides results in assembly into a trimeric antigen binding molecule with three antigen binding moieties on each terminus. The trimeric antigen binding molecule is hence a hexavalent antigen binding molecule. In one embodiment the three antigen binding moieties fused to the N-terminus are each specific for the same antigen, and the three antigen binding moieties fused to the C-terminus are each specific for another, different antigen; i.e. the trimeric antigen binding molecule is bispecific and trivalent for each specifity. As outlined above, the trivalency results in synergistic affinities of each antigen binding moiety, resulting in increased avidity of the trimeric antigen binding molecule. Hence the bispecific trimeric antigen molecule binds to both antigens with a high affinity compared to conventional IgG based bispecific antibodies.

In one embodiment the bispecific trimeric antigen binding molecule is capable of binding to a first cell surface antigen with the first antigen binding moiety and is capable of binding to a second, different cell surface antigen with the second antigen binding moiety. In one embodiment at least one of the cell surface antigens is a tumor cell antigen In one embodiment the bispecific trimeric antigen binding molecule is capable of binding to a cell surface antigen with the first antigen binding moiety and is capable of binding to a hapten with the second antigen binding moiety. Hence the bispecific trimeric antigen binding molecule can direct a hapten bound to the second antigen binding moiety to a target site, for example to a specific type of tumor cell or tumor stroma bearing the antigenic determinant. The hapten could be fluorescently or otherwise labeled to allow tracking of the bispecific trimeric antigen binding molecule to the target cell. Hence the bispecific trimeric antigen binding molecule could be used to diagnose or identify tumor cells in vitro and in vivo.

Haptens useful in this context are digoxygenin (DIG), biotin, or dinitrophenol.

The trimeric antigen binding molecule of the invention comprises three fusion polypeptides, each comprising at least one antigen binding moiety fused to a trimerization domain derived from human cartilage matrix protein. The fusion can be a direct bond between the trimerization domain and the antigen binding moiety (ies), or the trimerization domain and the antigen binding moiety (ies) can be connected through a linker. In a preferred embodiment the trimerization domain and the antigen binding moiety(ies) are connected through a peptide linker.

The term "linker" as used herein refers to a peptide linker and is preferably a peptide with an amino acid sequence with a length of at least 5 amino acids, preferably with a length of 5 to 100, more preferably of 10 to 50 amino acids. In one embodiment said peptide linker is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is (G4S)2.

The antigen binding moiety of the invention may be an antibody, or an antibody fragment.

In one embodiment said antigen binding moiety is an antibody fragment, selected from the group consisting of a Fab molecule, a Crossover Fab molecule, a single chain Fab molecule, an Fv molecule, a scFv molecule and a single domain antibody.

In one embodiment the antigen binding moiety is fused at its C-terminal amino acid to the N-terminal amino acid of said trimerization domain, optionally through a peptide linker.

In one embodiment at least one antigen binding moiety of the trimeric antigen binding molecule is a Fab molecule. As used herein, "Fab molecule" or "Fab fragment" refers to an antibody fragment comprising a light chain fragment comprising a VL domain and a constant domain of a light chain (CL), and a VH domain and a first constant domain (CH1) of a heavy chain. In one embodiment each of the three fusion polypeptides comprises a CMP trimerization domain and at least one Fab molecule. In one embodiment each of the three fusion polypeptides comprises a CMP trimerization domain and one Fab molecule. The Fab molecule may be fused to the N or C-terminus of the CMP trimerization domain. The Fab molecule can be fused at its heavy or light chain to the CMP trimerization domain. In one embodiment the Fab molecule is fused to the CMP trimerization domain through a peptide linker. In one embodiment the Fab molecule is fused at its C-terminal or N-terminal amino acid of the Fab heavy chain to the N-terminal amino acid of the CMP trimerization domain, optionally through a peptide linker. The resulting fusion polypeptide has the following structure (CMP trimerization domain)-(CH1VH) or (CMP trimerization domain)-(VHCH1), respectively. In one embodiment said Fab molecule is fused to the CMP trimerization domain through a linker, and the fusion polypeptide has the following structure (CMP trimerization domain)-linker-(CH1VH) or (CMP trimerization domain)-linker-(VHCH1), respectively. In one embodiment the trimeric antigen binding molecule comprises three fusion polypeptides as described above and three light chains (VLCL) of the Fab molecules that pair with the heavy chains VHCH1 of the fusion polypeptide.

In one embodiment of the invention at least one antigen binding moiety of the trimeric antigen binding molecule is a Fab molecule, wherein either the variable regions or the constant regions of the heavy and light chain are exchanged. Due to the exchange of either the variable regions or the constant regions, said Fab molecule is also referred to as "cross-Fab molecule" or "xFab molecule" or "crossover Fab molecule". Two different chain compositions of a crossover Fab molecule are possible and comprised in the antigen binding moieties useful in the trimeric antigen binding molecules of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab (VLVH). On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab (CLCH1). For clarity, in a crossover Fab molecule wherein the variable regions of the Fab light chain and the Fab heavy chain are exchanged (i.e. CrossFab (VLVH)) the peptide chain comprising the heavy chain constant region is referred to herein as the "heavy chain" of the crossover Fab molecule. Conversely, in a crossover Fab molecule wherein the constant regions of the Fab light chain and the Fab heavy chain are exchanged (i.e. CrossFab (CLCH1)), the peptide chain comprising the heavy chain variable region is referred to herein as the "heavy chain" of the crossover Fab molecule.

In one embodiment each of the three fusion polypeptides comprises a CMP trimerization domain and at least one cross-Fab molecule. In one embodiment each of the three fusion polypeptides comprises a CMP trimerization domain and one cross-Fab molecule. The cross-Fab molecule may be fused to the N or C-terminus of the CMP trimerization domain. The cross-Fab molecule can be fused at its heavy or light chain to the CMP trimerization domain. In one embodiment the cross-Fab molecule is fused to the CMP trimerization domain through a peptide linker. In one embodiment the cross-Fab molecule is fused at its C-terminal or N-terminal amino acid of the cross-Fab heavy chain to the N-terminal amino acid of the CMP trimerization domain, optionally through a peptide linker. In case of a CrossFab (VLVH), the resulting fusion polypeptide has the following structure (CMP trimerization domain)-(VLCH1) or (CMP trimerization domain)-(CH1VL), respectively. In one embodiment said Fab molecule is fused to the CMP trimerization domain through a linker, and the fusion polypeptide has the following structure (CMP trimerization domain)-linker-(VLCH1) or (CMP trimerization domain)-linker-(CH1VL), respectively.

In one embodiment the trimeric antigen binding molecule comprises three fusion polypeptides as described above and three light chains (VHCL) of the CrossFab (VLVH) molecules that pair with the heavy chains VLCH1 of the fusion polypeptide.

In case of a CrossFab (CLCH1), the resulting fusion polypeptide has the following structure (CMP trimerization domain)-(VHCL) or (CMP trimerization domain)-(CLVH), respectively. In one embodiment said Fab molecule is fused to the CMP trimerization domain through a linker, and the fusion polypeptide has the following structure (CMP trimerization domain)-linker-(VHCL) or (CMP trimerization domain)-linker-(CLVH), respectively.

In one embodiment the trimeric antigen binding molecule comprises three fusion polypeptides as described above and three light chains (VLCH1) of CrossFab (CLCH1) molecules that pair with the heavy chains VHCL of the fusion polypeptide.

In one embodiment of the invention at least one antigen binding moiety of the trimeric antigen binding molecule is a single chain Fab molecule. A "single chain Fab molecule" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids Said single chain Fab molecules a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering). The term "N-terminus" denotes the last amino acid of the N-terminal end of the amino acid sequence. The term "C-terminus" denotes the last amino acid of the C-terminal end of the amino acid sequence.

In one embodiment each of the three fusion polypeptides comprises a CMP trimerization domain and at least one single chain Fab molecule. In one embodiment each of the three fusion polypeptides comprises a CMP trimerization domain and one single chain Fab molecule. The single chain Fab molecule may be fused to the N or C-terminus of the CMP trimerization domain. In one embodiment the single chain Fab molecule is fused to the CMP trimerization domain through a peptide linker. In one embodiment the Fab molecule is fused at its C-terminal or N-terminal amino acid of the Fab heavy chain to the N-terminal amino acid of the CMP trimerization domain, optionally through a peptide linker. The resulting fusion polypeptide has the following structure a) (CMP trimerization domain)-(VH-CH1-linker-VL-CL) or b) (CMP trimerization domain)-(VL-CL-linker-VH-CH1) or c) (CMP trimerization domain)-(VH-CL-linker-VL-CH1) or d) (CMP trimerization domain)-(VL-CH1-linker-VH-CL), respectively. In one embodiment said Fab molecule is fused to the CMP trimerization domain through a linker, and the fusion polypeptide has the following structure a) (CMP trimerization domain)-linker-(VH-CH1-linker-VL-CL) or b) (CMP trimerization domain)-linker-(VL-CL-linker-VH-CH1) or c) (CMP trimerization domain)-linker-(VH-CL-linker-VL-CH1) or d) (CMP trimerization domain)-linker-(VL-CH1-linker-VH-CL), respectively.

In one embodiment of the invention at least one antigen binding moiety of the trimeric antigen binding molecule is a Fv molecule.

In one embodiment of the invention at least one antigen binding moiety of the trimeric antigen binding molecule is a single chain Fv molecule.

In addition to the antibody fragments outlined above, antigen binding moieties composed only of heavy chains could also be used in the trimeric antigen binding molecule of the invention. The antigen-binding site of these unusual heavy chain antibodies is formed only by a single domain, designated VHH, or aVH (autonomous variable heavy chain) or single domain variable heavy chain. Single domain variable heavy chains are easily produced as recombinant proteins. Other advantageous features of single domain variable heavy chains include their small size, high solubility, thermal stability, refolding capacity, and good tissue penetration. Single domain antibodies are described e.g. in Wesolowski et al, Med Microbiol Immunol (2009) 198:157-174. Methods of producing single domain variable heavy chain antibodies are described e.g. in WO2012152823 and WO2012056000 which is included therein by reference in its entirety.

These single domain variable heavy chain antibodies lack light chains and can also lack the CH1-domain. Therefore, the antigen-binding site of single domain variable heavy chain antibodies is formed only by a single domain.

In one embodiment of the invention at least one antigen binding moiety of the trimeric antigen binding molecule is a single domain antibody.

There are, beside antibodies, other binding proteins or binding domains that can be used to specifically bind a target molecule (e.g. Binz, H. K., Amstutz, P. and Pluckthun, A., Nat. Biotechnol. 23, 1257-1268, 2005). One such novel class of binding proteins or binding domains are based on designed repeat proteins or designed repeat domains (WO 2002/020565; Binz, H. K., Amstutz, P., Kohl, A., Stumpp, M. T., Briand, C, Forrer, P., Grutter, M. G., and Pluckthun, A., Nat. Biotechnol. 22, 575-582, 2004; Stumpp, M. T., Binz, H. K and Amstutz, P., Drug Discov. Today 13, 695-701, 2008).

Ankyrin repeat proteins have been identified in 1987 through sequence comparisons between four such proteins in *Saccharomyces cerevisiae, Drosophila melanogaster* and *Caenorhabditis elegans*. Breeden and Nasmyth reported multiple copies of a repeat unit of approximately 33 residues in the sequences of swi6p, cdcl0p, notch and lin-12 (Breeden and Nasmyth, 1987). The subsequent discovery of 24 copies of this repeat unit in the ankyrin protein led to the naming of this repeat unit as the ankyrin repeat (Lux et al., 1990). Later, this repeat unit has been identified in several hundreds of proteins of different organisms and viruses (Bork, 1993; SMART database, Schultz et al., 2000). These proteins are located in the nucleus, the cytoplasm or the extracellular space. This is consistent with the fact that the ankyrin repeat domain of these proteins is independent of disulfide bridges and thus independent of the oxidation state of the environment. The number of repeat units per protein varies from two to more than twenty (SMART database, Schultz et al., 2000). A minimum number of repeat units seems to be required to form a stable folded domain (Zhang and Peng, 2000). On the other hand, there is also some evidence for an upper limit of six repeat units being present in one folded domain (Michaely and Bennet, 1993).

WO 2002/020565 describes how large libraries of ankyrin repeat proteins can be constructed and their general application. These designed repeat domains harness the modular nature of repeat proteins and possess N-terminal and C-terminal capping modules to prevent the designed repeat domains from aggregation by shielding the hydrophobic core of the domain (Forrer, P., Stumpp, M. T., Binz, H. K. and Pluckthun, A., FEBS letters 539, 2-6, 2003). WO 2012069655 describes optimized repeat proteins by improving the C- or N-terminal capping modules or C- or N-terminal capping repeats of designed ankyrin repeat domains.

In one embodiment of the invention at least one antigen binding moiety of the trimeric antigen binding molecule is a binding protein comprising at least one ankyrin repeat motiv.

In one embodiment the trimeric antigen binding molecule comprises three fusion polypeptides each comprising two antigen binding moieties fused to a CMP trimerization domain. In one embodiment the trimeric antigen binding molecule comprises three fusion peptides wherein a first antigen binding moiety is fused to the CMP trimerisation domain on the N-terminus, and a second antigen binding moiety is fused to the C-terminus of the CMP trimerisation domain. The second antigen binding moieties may be an antibody or an antibody fragment. In one embodiment, said second antigen binding moiety is an antibody fragment, selected from the group consisting of a Fab molecule, a Crossover Fab molecule, a single chain Fab molecule, an Fv molecule, a scFv molecule and a single domain antibody. In one embodiment, said first antigen binding moiety is an antibody fragment and said second antigen binding moiety is an antibody fragment. Preferably, the second antigen binding moiety is a different antibody fragment than the first antigen binding moiety.

In one embodiment said first antigen binding moiety is a Fab molecule and said second antigen binding moiety is a single chain Fv molecule.

In one embodiment the trimeric antigen binding molecule comprises three fusion polypeptides each comprising a Fab molecule capable of specifically binding to a first antigen and a single chain Fv molecule capable of specifically binding to a second antigen.

In one embodiment each fusion polypeptide comprises a Fab molecule that is fused at the C-terminus of the Fab heavy chain to the N-terminus of the CMP trimerisation domain, optionally via a peptide linker, and a single chain Fv molecule that is fused at its N-terminus to the C-terminus of the CMP trimerisation domain, optionally via a peptide linker. Accordingly each of the three fusion polypeptides could for example have the following structure: (VHCH1)-(CMP trimerization domain)-scFv. In embodiments where the antigen binding domains are fused to the CMP trimerization domain via a peptide linker, the fusion polypeptides could for example have the following structure: (VHCH1)-linker-(CMP trimerization domain)-linker-scFv. In other embodiments only the Fab molecule is fused to the CMP trimerization domain via a peptide linker, and the scFv molecule is fused directly to the CMP trimerization domain, or vice versa. In one embodiment the trimeric antigen binding molecule comprises three fusion polypeptides as described above and three light chains (VLCL) that pair with the heavy (VHCH1) chains of the fusion polypeptide.

In one embodiment each fusion polypeptide comprises a Fab molecule that is fused at the C-terminus of the Fab light chain to the N-terminus of the CMP trimerisation domain, optionally via a peptide linker, and a single chain Fv molecule that is fused at its N-terminus to the C-terminus of the CMP trimerisation domain, optionally via a peptide linker. Accordingly each of the three fusion polypeptides could for example have the following structure: (VLCL)-(CMP trimerization domain)-scFv. In embodiments where the antigen binding domains are fused to the CMP trimerization domain via a peptide linker, the fusion polypeptides could for example have the following structure: (VLCL)-linker-(CMP trimerization domain)-linker-scFv. In other embodiments only the Fab molecule is fused to the CMP trimerization domain via a peptide linker, and the scFv molecule is fused directly to the CMP trimerization domain, or vice versa. In one embodiment the trimeric antigen binding molecule comprises three fusion polypeptides as described above and three heavy chains (VHCH1) that pair with the light (VLCL) chains of the fusion polypeptide.

In one embodiment the trimeric antigen binding molecule comprises three fusion polypeptides each comprising a Fab molecule capable of specifically binding to a first antigen and a crossFab molecule capable of specifically binding to a second antigen.

In one embodiment each fusion polypeptide comprises a Fab molecule that is fused at the C-terminus of the Fab heavy chain to the N-terminus of the CMP trimerisation domain, optionally via a peptide linker, and a crossFab molecule that is fused to the C-terminus of the CMP trimerisation domain, optionally via a peptide linker. Accordingly each of the three fusion polypeptides could for example have the following structure: (VHCH1)-(CMP trimerization domain)-(VLCH1) or (VHCH1)-(CMP trimerization domain)-(CLVH). In embodiments where the antigen binding domains are fused to the CMP trimerization domain via a peptide linker, the fusion polypeptides could for example have the following structure: (VHCH1)-linker-(CMP trimerization domain)-linker-(VLCH1) or (VHCH1)-linker-(CMP trimerization domain)-linker-(CLVH). In other embodiments only the Fab molecule is fused to the CMP trimerization domain via a peptide linker, and the cross-Fab molecule is fused directly to the CMP trimerization domain, or vice versa. In one embodiment the trimeric antigen binding molecule comprises three fusion polypeptides as described above, three light (VLCL) that pair with the heavy (VHCH1) chains of the fusion polypeptide and three (CLVH) or (VHCH1) chains that pair with the Crossfab part of the fusion polypeptide.

In one embodiment each fusion polypeptide comprises a Fab molecule that is fused at the C-terminus of the Fab light chain to the N-terminus of the CMP trimerisation domain, optionally via a peptide linker, and a cross-Fab molecule that is fused to the C-terminus of the CMP trimerisation domain, optionally via a peptide linker. Accordingly each of the three fusion polypeptides could for example have the following structure: (VLCL)-(CMP trimerization domain)-(VLCH1) or (VLCL)-(CMP trimerization domain)-(VHCL). In embodiments where the antigen binding domains are fused to the CMP trimerization domain via a peptide linker, the fusion polypeptides could for example have the following structure: (VLCL)-linker-(CMP trimerization domain)-linker-(VLCH1) or (VLCL)-linker-(CMP trimerization domain)-linker-(VHCL). In other embodiments only the Fab molecule is fused to the CMP trimerization domain via a peptide linker, and the cross-Fab molecule is fused directly to the CMP trimerization domain, or vice versa. In one embodiment the trimeric antigen binding molecule comprises three fusion polypeptides as described above, three heavy chains (VHCH1) that pair with the light (VLCL) chains of the fusion polypeptide and three (CLVH) or (VHCH1) chains that pair with the Crossfab part of the fusion polypeptide.

In one embodiment the trimeric antigen binding molecule comprises three fusion polypeptides comprising a sequence of SEQ ID NO.: 4 and SEQ ID NO.: 9.

In one embodiment the trimeric antigen binding molecule comprises three fusion polypeptides comprising a sequence of SEQ ID NO.: 5, SEQ ID NO.: 9 and SEQ ID No.: 10.

In one embodiment the trimeric antigen binding molecule comprises three fusion polypeptides comprising a sequence of SEQ ID NO.: 6 and SEQ ID No.: 9.

In one embodiment the trimeric antigen binding molecule comprises three fusion polypeptides comprising a sequence of SEQ ID NO.: 19 and SEQ ID No.: 20.

Recombinant Methods

Trimeric bispecific antigen binding molecules of the invention may be obtained, for example, by solid-state peptide synthesis (e.g. Merrifield solid phase synthesis) or recombinant production. For recombinant production one or more polynucleotide encoding the trimeric antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a trimeric antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the trimeric antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the trimeric antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit α-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the trimeric antigen binding molecule is desired, DNA encoding a signal sequence may be placed upstream of the nucleic acid encoding a trimeric antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the trimeric antigen binding molecule may be included within or at the ends of the trimeric antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a trimeric antigen binding molecule of the invention. As used herein, the term "host cell" refers to any kind of cellular system which can be engineered to generate the trimeric antigen binding molecules of the invention or fragments thereof. Host cells suitable for replicating and for supporting expression of trimeric antigen binding molecules are well known in the art. Such cells may be transfected or transduced as appropriate with the particular expression vector and large quantities of vector containing cells can be grown for seeding large scale fermenters to obtain sufficient quantities of the trimeric antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TM cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a trimeric antigen binding molecule according to the invention is provided, wherein the method comprises culturing a host cell comprising a polynucleotide encoding the trimeric antigen binding molecule, as provided herein, under conditions suitable for expression of the trimeric antigen binding molecule, and recovering the trimeric antigen binding molecule from the host cell (or host cell culture medium).

The components of the trimeric antigen binding molecule are genetically fused to each other. Trimeric antigen binding molecule can be designed such that its components are fused directly to each other or indirectly through a linker sequence. The composition and length of the linker may be determined in accordance with methods well known in the art and may be tested for efficacy. Examples of linker sequences between different components of trimeric antigen binding molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the trimeric antigen binding molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the trimeric antigen binding molecules of the invention. Non-limiting antibodies, antibody fragments, antigen binding domains or variable regions useful in the present invention can be of murine, primate, or human origin. If the trimeric antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the Trimeric antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CD3) is incubated in a solution comprising a first labeled antibody that binds to the antigen (e.g. V9 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

T cell activating bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the Trimeric antigen binding molecule binds. For example, for affinity chromatography purification of trimeric antigen binding molecules of the invention, a matrix with protein A or protein G may be used. Sequential Protein A or G affinity chromatography and size exclusion chromatography can be used to isolate a trimeric antigen binding molecule essentially as described in the Examples. The purity of the trimeric antigen binding molecule can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE. Three bands were resolved at approximately Mr 25,000, Mr 50,000 and Mr 75,000, corresponding to the predicted molecular weights of the Trimeric antigen binding molecule light chain, heavy chain and heavy chain/light chain fusion protein.

Assays

T cell activating bispecific antigen binding molecules provided herein may be identified, screened for, or characterized for their physical/chemical properties and/or biological activities by various assays known in the art.

Affinity Assays

The affinity of the Trimeric antigen binding molecule for an Fc receptor or a target antigen can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of trimeric antigen binding molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NETS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody. The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the trimeric antigen binding molecules of the invention can be measured by various assays as described in the Examples. Biological activities may for example include the induction of lysis of target cells such as tumor cells, and the induction of tumor regression and/or the improvement of survival.

Compositions, Formulations, and Routes of Administration

In a further aspect, the invention provides pharmaceutical compositions comprising any of the trimeric antigen binding molecules provided herein, e.g., for use in any of the below therapeutic methods. In one embodiment, a pharmaceutical composition comprises any of the trimeric antigen binding molecules provided herein and a pharmaceutically acceptable carrier. In another embodiment, a pharmaceutical composition comprises any of the trimeric binding molecules provided herein and at least one additional therapeutic agent, e.g., as described below.

Further provided is a method of producing a Trimeric antigen binding molecule of the invention in a form suitable for administration in vivo, the method comprising (a) obtaining a Trimeric antigen binding molecule according to the invention, and (b) formulating the Trimeric antigen binding molecule with at least one pharmaceutically acceptable carrier, whereby a preparation of Trimeric antigen binding molecule is formulated for administration in vivo.

Pharmaceutical compositions of the present invention comprise a therapeutically effective amount of one or more Trimeric antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one Trimeric antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Trimeric antigen binding molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the trimeric antigen binding molecules of the invention.

Parenteral compositions include those designed for administration by injection, e.g. subcutaneous, intradermal, intralesional, intravenous, intraarterial intramuscular, intrathecal or intraperitoneal injection. For injection, the trimeric antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the trimeric antigen binding molecules may be in powder form for constitution with a suitable vehicle, e.g., sterile pyrogen-free water, before use. Sterile injectable solutions are prepared by incorporating the trimeric antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the trimeric antigen binding molecules may also be formulated as a depot preparation. Such long acting formulations may be administered by implantation (for example subcutaneously or intramuscularly) or by intramuscular injection. Thus, for example, the trimeric antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the trimeric antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The trimeric antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the trimeric antigen binding molecules provided herein may be used in therapeutic methods. Trimeric antigen binding molecules of the invention can be used as immunotherapeutic agents, for example in the treatment of cancers.

For use in therapeutic methods, trimeric antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, trimeric antigen binding molecules of the invention for use as a medicament are provided. In further aspects, trimeric antigen binding molecules of the invention for use in treating a disease are provided. In certain embodiments, trimeric antigen binding molecules of the invention for use in a method of treatment are provided. In one embodiment, the invention provides a Trimeric antigen binding molecule as described herein for use in the treatment of a disease in an individual in need thereof. In certain embodiments, the invention provides a Trimeric antigen binding molecule for use in a method of treating an individual having a disease comprising administering to the individual a therapeutically effective amount of the trimeric antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a Trimeric antigen binding molecule as described herein for use in inducing lysis of a target cell, particularly a tumor cell. In certain embodiments, the invention provides a Trimeric antigen binding molecule for use in a method of inducing lysis of a target cell, particularly a tumor cell, in an individual comprising administering to the individual an effective amount of the Trimeric antigen binding molecule to induce lysis of a target cell. An "individual" according to any of the above embodiments is a mammal, preferably a human.

In a further aspect, the invention provides for the use of a Trimeric antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a Trimeric antigen binding molecule of the invention. In one embodiment a composition is administered to said individual, comprising the Trimeric antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a Trimeric antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the Trimeric antigen binding molecule may not provide a cure but may only provide partial benefit. In some embodiments, a physiological change having some benefit is also considered therapeutically beneficial. Thus, in some embodiments, an amount of Trimeric antigen binding molecule that provides a physiological change is considered an "effective amount" or a "therapeutically effective amount". The subject, patient, or individual in need of treatment is typically a mammal, more specifically a human.

In some embodiments, an effective amount of a Trimeric antigen binding molecule of the invention is administered to a cell. In other embodiments, a therapeutically effective amount of a Trimeric antigen binding molecule of the invention is administered to an individual for the treatment of disease.

For the prevention or treatment of disease, the appropriate dosage of a Trimeric antigen binding molecule of the invention (when used alone or in combination with one or more other additional therapeutic agents) will depend on the type of disease to be treated, the route of administration, the body weight of the patient, the type of trimeric antigen binding molecule, the severity and course of the disease, whether the trimeric antigen binding molecule is administered for preventive or therapeutic purposes, previous or concurrent therapeutic interventions, the patient's clinical history and response to the trimeric antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The trimeric antigen binding molecule is suitably administered to the patient at one time or over a series of treatments. Depending on the type and severity of the disease, about 1 µg/kg to 15 mg/kg (e.g. 0.1 mg/kg-10 mg/kg) of Trimeric antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the Trimeric antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the trimeric antigen binding molecule). An initial higher loading dose, followed by one or more lower doses may be administered. However, other dosage regimens may be useful. The progress of this therapy is easily monitored by conventional techniques and assays.

The trimeric antigen binding molecules of the invention will generally be used in an amount effective to achieve the intended purpose. For use to treat or prevent a disease condition, the trimeric antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the trimeric antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the trimeric antigen binding molecules may not be related to plasma concentration. One having skill in the art will be able to optimize therapeutically effective local dosages without undue experimentation.

A therapeutically effective dose of the trimeric antigen binding molecules described herein will generally provide therapeutic benefit without causing substantial toxicity. Toxicity and therapeutic efficacy of a Trimeric antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Trimeric antigen binding molecules that exhibit large therapeutic indices are preferred. In one embodiment, the Trimeric antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with trimeric antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The trimeric antigen binding molecules of the invention may be administered in combination with one or more other agents in therapy. For instance, a Trimeric antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disrupter, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of Trimeric antigen binding molecule used, the type of disorder or treatment, and other factors discussed above. The trimeric antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the Trimeric antigen binding molecule of the invention can occur prior to, simultaneously, and/or following, administration of the additional therapeutic agent and/or adjuvant. trimeric antigen binding molecules of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a Trimeric antigen binding molecule of the invention. The label or package insert indicates that the composition is used for treating the condition of choice. Moreover, the article of manufacture may comprise (a) a first container with a composition contained therein, wherein the composition comprises a Trimeric antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

General Methods
Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, 5$^{th}$ ed., NIH Publication No. 91-3242.

DNA Sequencing

DNA sequences were determined by di-deoxy sequencing.

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Example 1: Production and Purification of Trimeric Monospecific Antigen Binding Molecules Comprising a CMP Derived Trimerization Domain To enhance binding of Fab molecules to specific targets (especially to members of the TNFR-Super family) and for hereby enhanced cross-linking of these receptors, trimerized Fab molecules targeting human death receptor 5 (DR5, TRAIL-R2) were generated. The Fab genes (VHCH1) were fused to a short trimerization domain derived from human CMP (Uniprot Accession: P21941; Residues 454 to 496, SEQ ID NO.:2) by standard recombinant DNA technologies. The cysteine residues forming interchain disulfide bridges at positions 458 and 460 were used together with the coiled coil domain comprising residues 467 to 495.

Downstream of this domain a short FLAG tag sequence was added for easier detection of the protein. A common (Gly4Ser)2 linker was used to connect the Fab molecule with the trimerization domain. A scheme of this design is shown in FIG. 1a).

The VHCH1-CMP-FLAG sequence (and the corresponding VLCL sequence of the Fab) are operatively fused to a recombinant chimeric MPSV promoter for expression in mammalian cells. The used expression vectors also contain the oriP sequence for stable maintenance of plasmids in cells providing the Epstein Barr large nuclear antigen (EBNA). In addition a synthetic polyA signal sequence is located at the 3' end of the CDS.

All antibody expression vectors were generated using standard recombinant DNA technology as described in Sambrook, J. et al., Molecular cloning: A laboratory manual; Cold Spring Harbor Laboratory Press, Cold Spring Harbor, N.Y., 1989. Molecular biological reagents were used according the manufacturer's recommendations. Genes or gene fragments were either amplified by polymerase chain reaction (PCR) or generated from synthetic oligonucleotides at Geneart AG (Regensburg, Germany) by automated gene synthesis. PCR-amplified or subcloned DNA fragments were confirmed by DNA sequencing (Synergene GmbH, Switzerland). Plasmid DNA was transformed into and amplified in suitable E. coli host strains for preparation of transfection-grade plasmid DNA using standard Maxiprep kits (Qiagen). For production of the trimeric molecules HEK293 EBNA cells were transfected with plasmids encoding the respective genes using a standard polyethlenimine (PEI) based method. The used plasmid ratio of the two expression vectors was 1:1. Transfected cells were cultivated for 7 days before supernatants were harvested for purification. For the production in 500 ml shake flasks, 400 million HEK293 EBNA cells were seeded 24 hours before transfection. For transfection, cells were centrifuged for 5 min at 210×g, and supernatant was replaced by pre-warmed CD CHO medium. Expression vectors were mixed in 20 ml CD CHO medium to a final amount of 200 µg DNA. After addition of 540 µl PEI, the solution was vortexed for 15 s and incubated for 10 min at room temperature. Subsequently, cells were mixed with the DNA/PEI solution, transferred to a 500 ml shake flask and incubated for 3 hours at 37° C. in a humidified incubator with a 5% CO2 atmosphere. After the incubation time, 160 ml F17 medium was added and cells were cultivated for 24 hours. The production medium was supplemented with 5 µM kifunensine. One day after transfection 1 mM valproic acid and 7% Feed 1 (Lonza) were added. After 7 days of cultivation, supernatant was collected for purification by centrifugation for 15 min at 210 g. The solution was sterile filtered (0.22 µm filter), supplemented with sodium azide to a final concentration of 0.01% w/v, and kept at 4° C.

The secreted protein was purified from cell culture supernatants first by affinity chromatography, via CH1 domain of human IgG antibodies. The second chromatographic step was a size exclusion chromatography. For affinity chromatography, the supernatant was loaded on a column packed with CaptureSelect IgG-CH1 matrix (Column Volume=1 ml; BAC, The Netherlands) and equilibrated with 5 ml 50 mM Tris(hydroxymethyl)-aminomethan (TRIS), 100 mM Glycine, 150 mM sodium chloride, pH 8.0. Unbound protein was removed by washing with at least ten column volumes 50 mM TRIS, 100 mM Glycine, 150 mM sodium chloride, pH 8.0. The target protein was eluted in a linear pH-gradient over 20 column volumes from 50 mM TRIS, 100 mM Glycine, 150 mM sodium chloridepH 8.0 to pH 2.0. The column was subsequently washed with 10 column volume 50 mM TRIS, 100 mM Glycine, 150 mM sodium chloride, pH 2.0.

The protein solution was neutralized by adding 1/40 (v/v) of 2M Tris, pH8.0. followed by a concentration step. Finally, the protein was filtered prior to loading on a HiLoad Superdex 200 column (GE Healthcare) equilibrated with 20 mM Histidine, 140 mM sodium chloride, 0.01% (v/v) Tween-20 solution of pH 6.0.

Example 2: Characterisation of Trimeric Monospecific Antigen Binding Molecules Comprising a CMP Derived Trimerization Domain The protein concentration of the purified huCMP fusion proteins were determined by measuring the optical density (OD) at 280 nm, using the molar extinction coefficient calculated on the basis of the amino acid sequence.

Figure 2A:
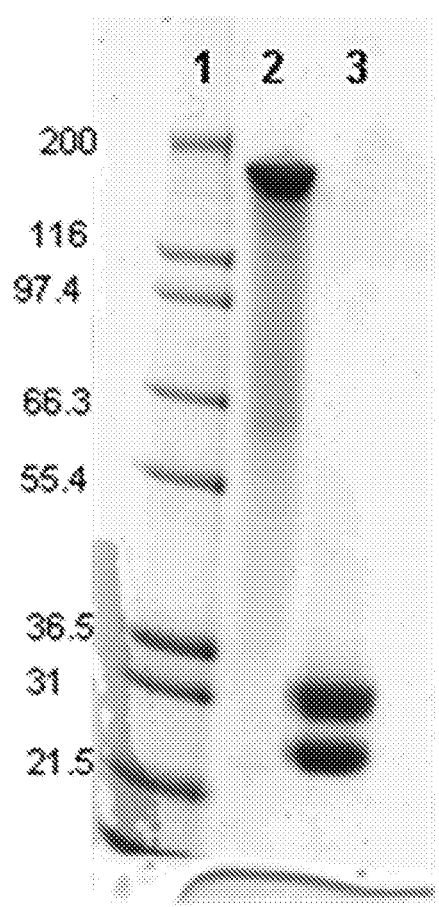
FIGS. 2A and 2B: SDS-PAGE.
Figure 2B:
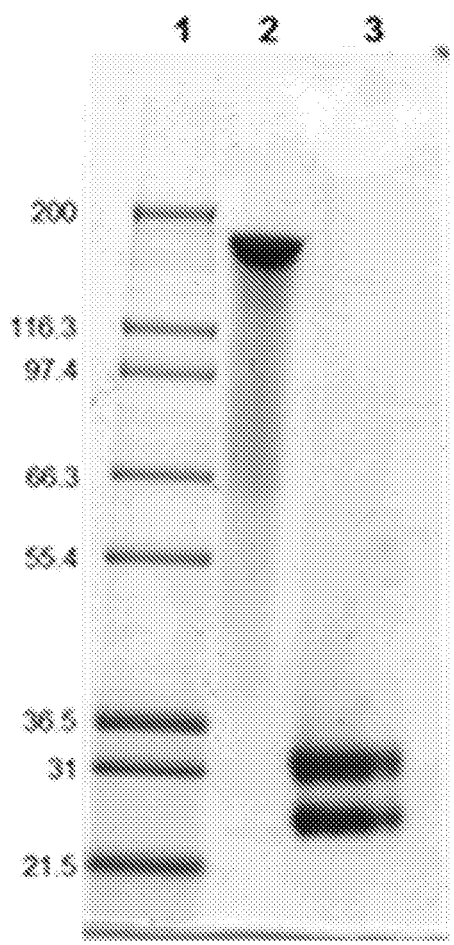
Figure 3:
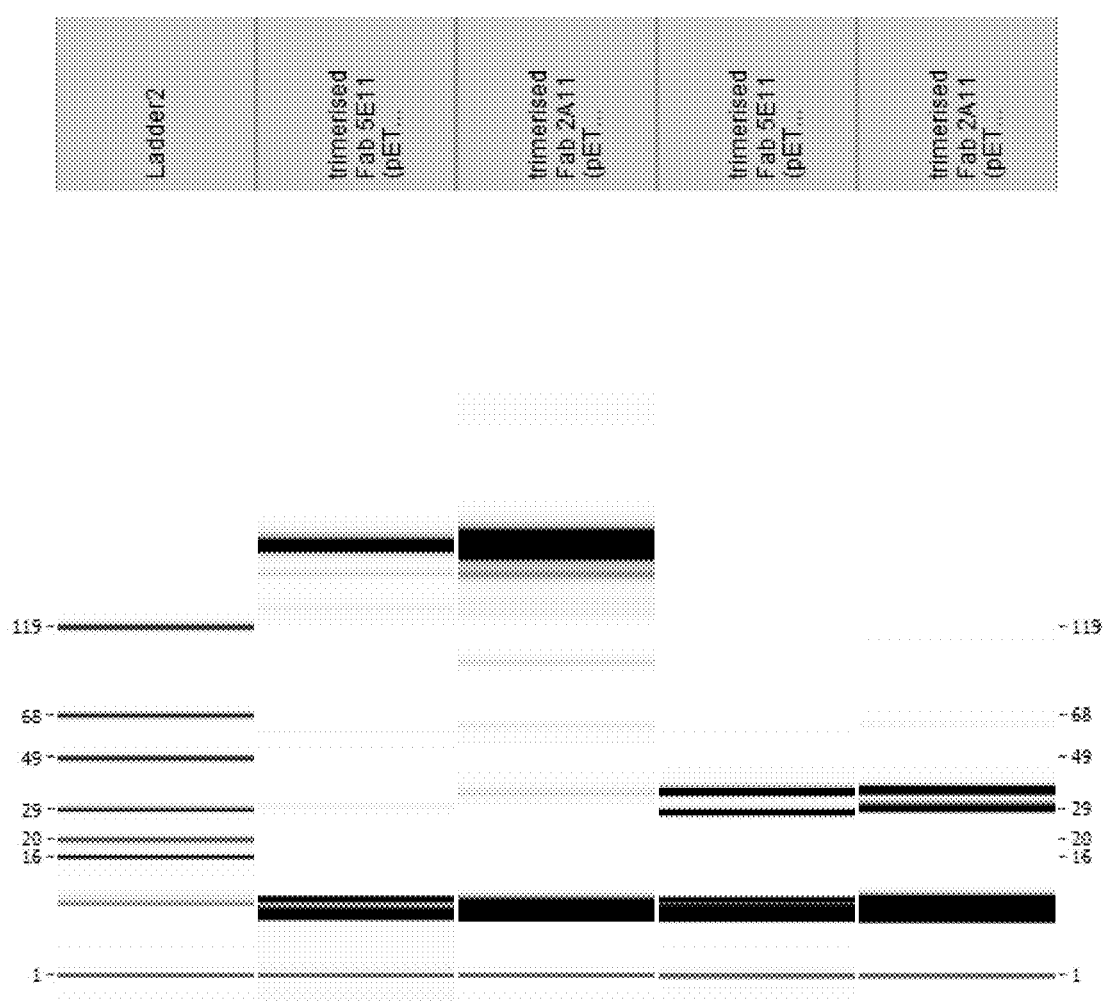
FIG. 3: CE-SDS analyses. Electropherogram shown as SDS-Page of trimerized huCMP anti-DR5 (5E11) Fab and trimerized huCMP anti-DR5 (2A11).

Purity and molecular weight of the huCMP containing construct was analyzed by SDS-PAGE in the presence and absence of a reducing agent (5 mM 1,4-dithiotreitol, DTT) and staining with Coomassie (SimpleBlue™ SafeStain from Invitrogen; FIG. 2). The NuPAGE® Pre-Cast gel system (Invitrogen, USA) was used according to the manufacturer's instructions (4-12% Tris-Acetate gels or 4-12% Bis-Tris). Purity and molecular weight of the huCMP containing construct was also analyzed by CE-SDS in the presence and absence of a reducing agent (Invitrogen) using a LabChipGXII (Caliper) (FIG. 3).

The aggregate content of the samples was analyzed using a TSKgel G3000 SW XL analytical size-exclusion column (Tosoh) equilibrated in 25 mM K2HPO4, 125 mM NaCl, 200 mM L-Arginine Monohydrocloride, 0.02% (w/v) NaN3, pH 6.7 running buffer at 25° C.

The molecular weight of the huCMP containing construct was determined under non-reducing and reducing conditions by LC-MS using a Agilent HPLC 1200 coupled to a TOF 6441 mass spectrometer (Agilent). For analyses under reduced conditions sample was incubated for 30 minutes at 37° C. in 10 µl 8 M Guanidine-HCl and 10 µl 0.5 mM TCEP diluted in 4 M Guanidine-HCl. Non-reduced samples were directly used for LC-MS analyses. The chromatographic separation was performed on a Macherey Nagel Polysterene column; RP1000-8 (8 µm particle size, 4.6×250 mm; cat. No. 719510) using the program shown in table 1. Eluent A was 5% acetonitrile and 0.05% (v/v) formic acid in water, eluent B was 95% acetonitrile, 5% water and 0.05% formic acid. The separation was performed at 40° C. with a flow of 1 ml/min and 7 (15 µl) of the sample was injected.

During the first 4 minutes the eluate is directed into the waste to prevent the mass spectrometer from salt contamination. The ESI-source was running with a drying gas flow of 12 l/min, a temperature of 350° C. and a nebulizer pressure of 60 psi. The MS spectra are acquired using a fragmentor voltage of 350 V and a mass range 700 to 3200 m/z in positive ion mode. MS data are acquired by the instrument software from 4 to 17 minutes.

TABLE 1

Mixture of solvents in HPLC chromatography for separation of individual compounds for Mass Spectrometry analysis. Solvent A is: 5% acetonitrile and 0.05% (v/v) formic acid in water, and solvent B is: 95% acetonitrile, 5% water and 0.05% formic acid.

| Time (min.) | % B |
| --- | --- |
| 0.5 | 15 |
| 10 | 60 |
| 12.5 | 100 |
| 14.5 | 100 |
| 14.6 | 15 |
| 16 | 15 |
| 16.1 | 100 |

All used analytical method confirmed homogeneous preparation of trimerized molecules. Table 2 shows purity, and final monomer content and mass of the huCMP containing constructs. Table 3 shows yield and thermal stability in comparison to bispecific huCMP containing constructs.

TABLE 2

Biochemical analysis of monospecific huCMP containing constructs.

| Construct | SEC Trimer [%] | CE-SDS non red [%] | CE-SDS red [%] | LC/MS (non red) | LC/MS (red) |
|---|---|---|---|---|---|
| Trimerized huCMP anti-DR5 Fab (5E11) SEQ ID NO 4, 9 | 100% (341 kDa) | 97% (169 kDa) | 28% (38 kDa) 62% (34 kDa) | Expected: 159'414 Da Experimentally found: 159'748 Da | (VL-CL) Expected: 23'349 Da Experimentally found: 23'352 Da (VH-CH1-huCMP-flag) Expected: 29'819 Da Experimentally found: 29'905 Da |
| Trimerized huCMP anti-DR5 Fab (2A11) SEQ ID NO 3, 8 | 86% (322 kDa) | n.d. | 30% (29 kDa) 61% (35 kDa) | 161'278 Da | n.d. |

Trimer content of the purified molecules was determined by size exclusion chromatography (SEC), or via capillary electrophoresis in SDS gels (CE SDS). Mass spectrometry (LC/MS) determined the mass of the molecules after chromatographic separation of the individual components.

Example 3: Binding of Trimeric Monospecific Antigen Binding Molecules

Assessment of the binding capabilities of the trimerized anti-DR5 Fab was determined using a cell based FRET (Fluorescence Resonance Energy Transfer) assay (TagLite). For the preparation of huDR5 expressing cells, adherent HEK293 EBNA cells were transfected with a huDR5-SNAP construct containing the PDGFR Transmembrane domain using Lipofectamine. One day prior transfection $4 \times 10^6$ cells were seeded in a T75 flask and grown overnight in a humidified incubator under 5% CO2 atmosphere at 37° C. For transfection, 2 µg of plasmid DNA was mixed with 30 µl Lipofectamine 2000 (Invitrogen, Cat No 11668-019) and 4 ml OptiMEM medium (Gibco) and incubated for 20 min at RT. Cells were washed once with D-PBS (Gibco) and the transfection mix was added to the cells together with 6 ml of culture medium (DMEM containing Glutamax, 10% FCS and NEAA). After a 20 h incubation in a humidified incubator with 5° C. CO2 atmosphere at 37° C., the antigen expressed was labeled with the FRET donor by incubating the cells with 100 nM Lumi4-Tb (Cisbio) in 1× TagLite buffer (Cisbio) for 1 h at 37° C. in the incubator. After 4 wash steps with TagLite buffer, cells were detached using cell dissociation buffer, washed in TagLite buffer and the emission of the Tb from 10000 cells/well in a 384 well plate measured in the Victor3 fluorescence reader at 620 nm. The excitation wavelength was 343 nm. Cells were aliquoted and stored in freezing medium (culture medium supplemented with 10% DMSO) at −80° C. For performing an assay cells have to be thawed, washed once with TagLite buffer, resuspended in TagLite buffer to an appropriate cell number and pipetted straight in the assay wells.

To perform a competition assay the DR5 binder (as IgG) was labeled with the FRET acceptor (d2) using a d2 labeling kit (Cisbio) according to the manufacturers manual.

The competition assay was carried out in a 384 well format by adding 25 nM final concentration of the d2 labeled anti-DR5 to 1000 DR5-Tb expressing HEK293 EBNA cells per well followed by adding the unlabeled anti-DR5 or the anti-DR5 trimerized Fab in a 1:2 dilutions from 750 to 5.8 nM final in the well. Cells only served as a blank control. All samples were analyzed in duplicates. The plate was incubated for 2 h at RT and the emission signals of the Tb at 620 nm as well as of the d2 at 665 nm were measured with a Tecan Infinite 200 (Tecan). The 665 nm signal from each well was normalized to the 620 nm signal from the same well and the blank control subtracted.

Figure 4:
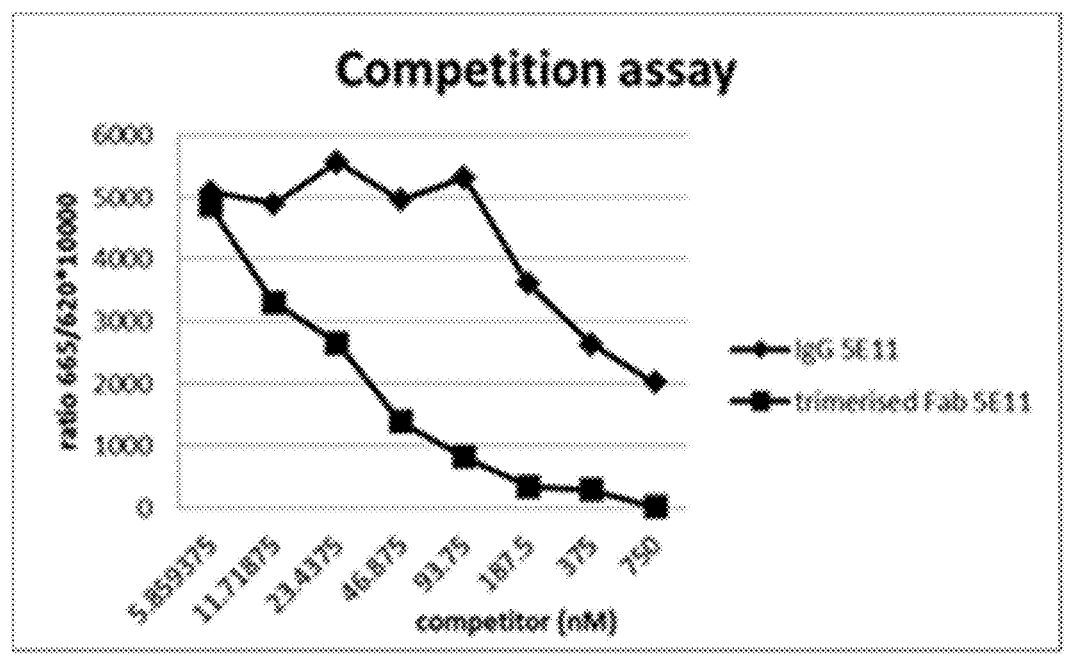
FIG. 4: TagLite. Comparison of the competition of trimerised anti-DR5 Fab 5E11 versus the same binder in bivalent IgG format on DR5 overexpressing target cells. Fluorescently labeled 5E11 IgG was added to the cells, and unlabeled dimeric (IgG) or trimeric 5E11 antibody was titrated to compete the fluorescence signal. The trimeric construct shows 50% competition at ~10-fold lower concentration than the IgG construct.

The competition assay shows that the trimerized Fab competes much stronger for the binding of the labeled IgG than the unlabeled IgG to huDR5 on the cell confirming a functional trimeric form of the construct (FIG. 4).

Example 4: Production and Purification of Trimeric Monospecific Antigen Binding Molecules Comprising a Collagen XV Derived Trimerization Domain In parallel to the experiment addressing the trimerization via the CMP domain, we tested the trimerization of Fabs using the collagen XV trimerization domain (Cuesta et al.; 2012, mAbs, Volume 4, Issue 2, 226-232). The design was essentially the same as for the CMP and having the Fab at the N-terminus followed by a short Gly-Ser linker before the trimerization domain followed by a FLAG tag. Expression was performed as described above in HEK293-EBNA cells. Unfortunately, the yields were very low and the product consisted mainly out of aggregates. (data not shown).

Example 5: Production and Purification of Bispecific, Hexavalent DR5-FAP Molecules for Targeted Cross-Linking of DR5

To evaluate the effect of hyper-cross-linking of DR5 via a second trimeric targeting moiety, a FAP (Fibroblast activation protein) specific binder was fused C-terminally to the trimerized DR5 Fab (5E11) construct. A scheme of this design is shown in FIG. 1b). Two different molecules were generated using the same FAP antibody (28H1) either as CrossFab (VHCL) or as disulfide stabilized scFv (H44/L100) fused via a (G4S)4 linker to the trimeric DR5 VHCH1 chain. The molecules were transiently produced in HEK293 EBNA cells (400 ml scale, PEI based transfection) and purified as follows: After a Capture Select IgG CH1 column the eluted antibodies were further purified by size exclusion chromatography (Superose 6 10/300 GL). A control molecule comprising trimeric FAP (28H1) CrossFab fused to the C-terminus of the CMP trimerization domain also was produced in HEK293 EBNA cells. All molecules were characterized with respect to product yield, quality and activity as described in example 2. Results are shown in table 3.

TABLE 3

Analysis of mono- or bispecific trimeric molecules

|  | Trimeric Bispecific molecule 5E11-28H1 CrossFab (SEQ ID NO 5, 9, 10) | Trimeric Bispecific molecule 5E11_28H1 scFv (SEQ ID NO 6, 9) | Trimeric Monospecific molecule 28H1 CrossFab (SEQ ID NO 7, 10) |
| --- | --- | --- | --- |
| Yield [mg/L] | 1.52 | 2.76 | 19.50 |
| Monomer [%] | 92.64 | 96.1 | 97.88 |
| HMW [%] | 2.85 | 0.00 | 1.23 |
| LMW [%] | 4.51 | 3.9 | 0.88 |
| Thermal stability [° C.] | 59 | 59 | 62 |

Thermal stability of the molecules was analyzed by Dynamic Light Scattering (DLS) experiment indicating a slight decrease of stability of the bispecific molecules compared to the monospecific one. In brief, 30 μg of filtered protein sample with a protein concentration of 1 mg/ml is applied in duplicate to a Dynapro plate reader (Wyatt Technology Corporation; USA). The temperature is ramped from 25 to 75° C. at 0.05° C./min, with the radius and total scattering intensity being collected.

Example 6: Cell-Based Target Binding of Mono and Bispecific Trimeric Antigen Binding Molecules To evaluate cell based target binding of the different molecules a FRET assay (TagLite, CisBio) was used in which either DR5 or FAP was expressed with a SNAP tag and a PDGFR transmembrane region (TM) for extracellular display. Binding was determined as competition with labeled anti DR5 or anti FAP IgG causing a reduction of FRET signal. A DR5 specific bivalent IgG antibody ("5E11 IgG") and a IgG antibody with two binding sites specific for DR5 to which two crossover Fab fragments specific for FAP are fused at the C-terminus (5E11_28H1 (2+2)) served as control molecules. As summarized in table 4 the 5E11 IgG and the 5E11_28H1 bispecific molecule (2+2 format) show a similar competition behavior, as expected. On the other hand, the trimeric 5E11 Fab and the bispecific DR5-FAP trimer containing the scFv also show very similar competition results but already with much lower antibody concentration indicating that these molecules bind with a higher avidity to DR5. In contrast, the bispecific trimeric Crossfab molecule shows a competition behavior somewhere in between these two groups indicating that it binds with higher avidity than the molecules with bivalent DR5 binding but with a lower avidity than the trimeric constructs.

TABLE 4

EC50 values for DR5 binding

|  | DR5 (5E11) IgG | DR5 (5E11) trimeric Fab SEQ ID NO 4, 9 | DR5 (5E11)-trimeric Fab - FAP (28H1) trimericCrossFab (SEQ ID NO 5, 9, 10) | DR5 (5E11)-trimeric Fab - FAP (28H1) trimeric scFv (SEQ ID NO 6, 9) | 5E11_28H1 (2 + 2) |
| --- | --- | --- | --- | --- | --- |
| EC50 [nM] 16 hrs | 134.2 | 5.4 | 18.5 | 5.0 | 282.9 |
| EC50 [nM] 5 hrs | 154.3 | 3.6 | 15.5 | 3.8 | n.d. |
| EC50 [nM] 3 hrs | 131.4 | 6.6 | n.d. | n.d. | 84.8 |

Figure 5:
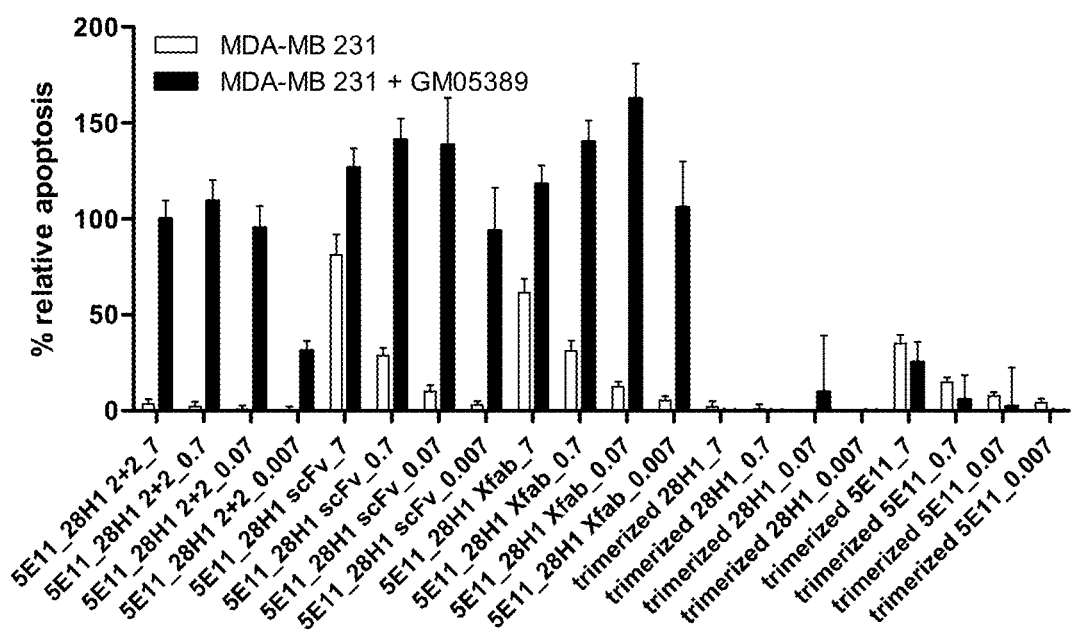
FIG. 5: Induction of apoptosis on MDA-MB-231 breast cancer cells as determined by DNA fragmentation in a Cell Death Detection ELISA. The assay was performed in the absence or presence of FAP expressing fibroblasts (GM05389) for hyper-cross-linking of the trimeric molecules.

To evaluate functional activity of bispecific trimerized DR5-FAP molecules induction of apoptosis of MDA-MB-231 breast cancer cells was determined in co-culture assays with the FAP expressing fibroblast cell line GM05389. Apoptosis of the target cell is induced by cross-linking of the death receptor DR5 and can be accomplished by agonistic DR5 antibodies. Since the degree of apoptosis is directly dependent on the hyper-cross-linking of DR5 it was assumed that binding to DR5 and an antigen expressed on a second cell (in this case the fibroblast cell-line), each in trivalent form would significantly increase apoptosis induction. FIG. 5 summarizes the comparison of DR5-FAP bispecific dimeric vs. bispecific trimeric molecules in terms of apoptosis activity. As control molecules the corresponding monospecific trimeric DR5 and FAP binder were used. The fibroblast cell-line GM05389 was seeded at a density of $10^4$ cells/well and incubated over night before bispecific constructs (and control molecules) were added in different concentrations. After additional incubation for 10 min for the constructs to bind to FAP 104 MDA-MB-231 cells were added and incubated for 24 hrs before apoptosis was determined using a cell death detection ELISA assay. The constructs were assayed in the presence or absence of FAP expressing fibroblasts. The DR5-FAP bispecific molecule in 2+2 format showed a decent apoptosis induction activity over a broad concentration range (7.0-0.07 nM) only in the presence of fibroblasts with a significant drop in activity at 0.007 nM. In contrast to that, at high concentrations, the bispecific trimeric molecules (both with CrossFab or scFv fused to the DR5 trimer) exhibited clear apoptosis activity already in the absence of FAP expressing GM05389. Further cross-linking via the fibroblast significantly increased apoptosis induction and even at the lowest concentration (0.007 nM) the trimerized constructs binding to DR5 and FAP showed very high activity. The control molecules (trimeric 5E11 and trimeric 28H1) showed only low and no apoptosis activity, respectively.

Example 7: Use of Trimeric Antigen Binding Molecule in Diagnostic Settings

Another trimerized molecule was generated by fusing the Fab fragment binding to Digoxigenin (described by Metz et al.; 2011, Proc Natl Acad Sci USA. 108(20):8194-8199) at the N-terminus of the CMP trimerization domain. At its C-terminus a scFv molecule capable of specifically binding to CEA (Carcinoembryonic antigen) was used for tumor targeting. The resulting molecule had SEQ ID NO 19 and 20. The final molecule consists only of two chains and does not require the introduction and optimization of the Cross-Mab technology as described in example 6. This molecule was cloned, expressed and purified as described above. Table 5 shows the results of analytical SEC after purification. It can be clearly seen that >98% of the material is of the monomeric fraction, and only <2% are some oligomeric species. This shows that the CMP domain can be used to create stable hexavalent constructs in the Fab-CMP-scFv format as well.

TABLE 5

Analytical SEC of Anti-Digoxigenin(Fab-HC)-CMP-anti-CEA(scFv)Digoxigenin

| No. UV_VIS_1 | Ret. Time UV_VIS_1 min | Peak Name UV_VIS_1 | Height UV_VIS_1 mAU | Area UV_VIS_1 mAU' min | Rel. Area UV_VIS_1 % | Conc. UV_VIS_1/ µl |
|---|---|---|---|---|---|---|
| 1 | 11.31 | Monomer | 1.63 | 0.85 | 1.71 | n.a. |
| 2 | 12.96 | Fragments | 100.44 | 48.99 | 98.29 | n.a. |

The following sequences are amino acid sequences comprised in the antigen binding molecules of the invention.

| Description | Protein sequence | Seq. ID # |
|---|---|---|
| Full length human CMP | MRVLSGTSLMLCSLLLLLQALCSPGLAPQSRGHLCRTR PIDLVFVVDSSRSVRPVEFEKVKVFLSQVIESLDVGPN ATRVGMVNYASTVKQEFSLRAHVSKAALLQAVRRIQPL STGTMTGLAIQFAITKAFGDAEGGRSRSPDISKVVIVV TDGRPQDSVQDVSARARASGVELFAIGVGSVDKATLRQ IASEPQDEHVDYVESYSVIEKLSRKFQEAFCVVSDLCA TGDHDCEQVCISSPGSYTCACHEGFTLNSDGKTCNVCS GGGGSSATDLVFLIDGSKSVRPENFELVKKFISQIVDT LDVSDKLAQVGLVQYSSSVRQEFPLGRFHTKKDIKAAV RNMSYMEKGTMTGAALKYLIDNSFTVSSGARPGAQKVG IVFIDGRSQDYINDAAKKAKDLGFKMFAVGVGNAVEDE LREIASEPVAEHYFYTADFKTINQIGKKLQKKICVEED PCACESLVKFQAKVEGLLQALTRKLEAVSKRLAILENT VV | 1 |
| CMP trimerization domain | CACESLVKFQAKVEGLLQALTRKLEAVSKRLAILENTV V | 2 |
| VHCH1-CMP-Flag DR5 clone 2A11 (Fab molecule specific for DR5 fused to N-terminus | MGWSCIILFLVATATGVHSEVQLLESGGGLVQPGGSLR LSCAASGFTFSSYAMSWVRQAPGKGLEWVSAISGSGGS TYYADSVKGRFTISRDNSKNTLYLQMNSLRAEDTAVYY CARGPYGRYAALDYWGQGTLVTVSSASTKGPSVFPLAP SSKSTSGGTAALGCLVKDYFPEPVTVSWNSGALTSGVH | 3 |

| Description | Protein sequence | Seq. ID # |
|---|---|---|
| of CMP trimerization domain) | TFPAVLQSSGLYSLSSVVTVPSSSLGTQTYICNVNHKP SNTKVDKKVEPKSCDGGGGSGGGGSEEDPCACESLVKF QAKVEGLLQALTRKLEAVSKRLAILENTVVASDYKDDD DKSG | |
| VHCH1-CMP-Flag DR5 clone 5E11 (Fab molecule specific for DR5 fused to N-terminus of CMP trimerization domain) | MGWSCIILFLVATATGVHSEVQLLESGGGLVQPGGSLR LSCAASGFTFSSYAMSWVRQAPGKGLEWVSAISGSGGS TYYADSVKGRFTISRDNSKNTLYLQMNSLRAEDTAVYY CAKGVRVSFDYWGQGTLVTVSSASTKGPSVFPLAPSSK STSGGTAALGCLVKDYFPEPVTVSWNSGALTSGVHTFP AVLQSSGLYSLSSVVTVPSSSLGTQTYICNVNHKPSNT KVDKKVEPKSCDGGGGSGGGGSEEDPCACESLVKFQAK VEGLLQALTRKLEAVSKRLAILENTVVASDYKDDDDKS G | 4 |
| DR5 (5E11) Fab molecule-CMP-_FAP (28H1) CrossFab VHCH1-CMP-VHCL (Fab molecule specific for DR5 fused to N-terminus of CMP trimerization domain, Crossfab molecule specific for FAP fused to C-terminus of CMP trimerization domain) | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCAKGVRVSFDYWGQGTLVT VSSASTKGPSVFPLAPSSKSTSGGTAALGCLVKDYFPE PVTVSWNSGALTSGVHTFPAVLQSSGLYSLSSVVTVPS SSLGTQTYICNVNHKPSNTKVDKKVEPKSCDGGGGSGG GGSEEDPCACESLVKFQAKVEGLLQALTRKLEAVSKRL AILENTVVASDYKDDDDKSGGGGSGGGGSGGGGSGGGG SEVQLLESGGGLVQPGGSLRLSCAASGFTFSSHAMSWV RQAPGKGLEWVSAIWASGEQYYADSVKGRFTISRDNSK NTLYLQMNSLRAEDTAVYYCAKGWLGNFDYWGQGTLVT VSSASVAAPSVFIFPPSDEQLKSGTASVVCLLNNFYPR EAKVQWKVDNALQSGNSQESVTEQDSKDSTYSLSSTLT LSKADYEKHKVYACEVTHQGLSSPVTKSFNRGEC | 5 |
| DR5 (5E11) Fab molecule-CMP-_FAP(28H1) scFv VHCH1-CMP-VHVL (Fab molecule specific for DR5 fused to N-terminus of CMP trimerization domain, scFv molecule specific for FAP fused to C-terminus of CMP trimerization domain) | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCAKGVRVSFDYWGQGTLVT VSSASTKGPSVFPLAPSSKSTSGGTAALGCLVKDYFPE PVTVSWNSGALTSGVHTFPAVLQSSGLYSLSSVVTVPS SSLGTQTYICNVNHKPSNTKVDKKVEPKSCDGGGGSGG GGSEEDPCACESLVKFQAKVEGLLQALTRKLEAVSKRL AILENTVVSGGGGSGGGGSGGGGSGGGGSEVQLLESGG GLVQPGGSLRLSCAASGFTFSSHAMSWVRQAPGKCLEW VSAIWASGEQYYADSVKGRFTISRDNSKNTLYLQMNSL RAEDTAVYYCAKGWLGNFDYWGQGTLVTVSSGGGGSGG GGSGGGGSGGGGSEIVLIQSPGILSLSPGERATLSCRA SQSVSRSYLAWYQQKPGQAPRLLIIGASTRATGIPDRF SGSGSGTDFTLTISRLEPEDFAVYYCQQGQVIPPTFGC GTKVEIK | 6 |
| CMP-FAP(28H1) CrossFab (Crossfab molecule specific for FAP fused to C-terminus of CMP trimerization domain) | GSEEDPCACESLVKFQAKVEGLLQALTRKLEAVSKRLA ILENTVVSGGGGSGGGGSGGGGSGGGGSEVQLLESGGG LVQPGGSLRLSCAASGFTFSSHAMSWVRQAPGKGLEWV SAIWASGEQYYADSVKGRFTISRDNSKNTLYLQMNSLR AEDTAVYYCAKGWLGNFDYWGQGTLVTVSSASVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC VLCL | 7 |
| DR5 clone 2A11 (Fab light chain specific for DR5) | MGWSCIILFLVATATGVHSDIQMTQSPSSLSASVGDRV TITCSASQGIRNYLNWYQQKPGKAPKLLIYYTSSLHSG VPSRFSGSGSGTDFTLTISSLQPEDFATYYCQQYSKLP WTFGQGTKVEIKRTVAAPSVFIFPPSDEQLKSGTASVV CLLNNFYPREAKVQWKVDNALQSGNSQESVTEQDSKDS TYSLSSTLTLSKADYEKHKVYACEVTHQGLSSPVTKSF NRGEC | 8 |
| VLCL DR5 clone 5E11 (Fab light chain specific for DR5) | MGWSCIILFLVATATGVHSEIVLTQSPGILSLSPGERA TLSCRASQSVSSSYLAWYQQKPGQAPRLLIYGASSRAT GIPDRFSGSGSGTDFTLTISRLEPEDFAVYYCQQGTTH PITFGQGTKVEIKRTVAAPSVFIFPPSDEQLKSGTASV VCLLNNFYPREAKVQWKVDNALQSGNSQESVTEQDSKD STYSLSSTLTLSKADYEKHKVYACEVTHQGLSSPVTKS FNRGEC | 9 |

-continued

| Description | Protein sequence | Seq. ID # |
|---|---|---|
| VLCH1<br>FAP clone 28H1<br>(crossFab VLCH1 chain specific for FAP) | EIVLIQSPGILSLSPGERATLSCRASQSVSRSYLAWYQ<br>QKPGQAPRLLIIGASTRATGIPDRFSGSGSGTDFTLTI<br>SRLEPEDFAVYYCQQGQVIPPTFGQGTKVEIKSSASTK<br>GPSVFPLAPSSKSTSGGTAALGCLVKDYFPEPVTVSWN<br>SGALTSGVHTFPAVLQSSGLYSLSSVVTVPSSSLGTQT<br>YICNVNHKPSNTKVDKKVEPKSCD | 10 |
| Anti-Digoxigenin(Fab-HC)-CMP-anti-CEA(scFv) | MGWSCIILFLVATATGVHSQVQLVESGGGLVKPGGSLR<br>LSCAASGFTFSDYAMSWIRQAPGKGLEWVSSINIGATY<br>IYYADSVKGRFTISRDNAKNSLYLQMNSLRAEDTAVYY<br>CARPGSPYEYDKAYYSMAYWGQGTIVIVSSASTKGPSV<br>FPLAPSSKSTSGGTAALGCLVKDYFPEPVTVSWNSGAL<br>TSGVHTFPAVLQSSGLYSLSSVVTVPSSSLGTQTYICN<br>VNHKPSNTKVDKKVEPKSCDKTHGGGGSGGGGSEEDPC<br>ACESLVKFQAKVEGLLQALTRKLEAVSKRLAILENTVV<br>GGGGSGGGGSQVKLEQSGAEVVKPGASVKLSCKASGFN<br>IKDSYMHWLRQGPGQCLEWIGWIDPENGDTEYAPKFQG<br>KATFTTDTSANTAYLGLSSLRPEDTAVYYCNEGTPTGP<br>YYFDYWGQGTLVTVSSGGGGSGGGGSGGGGSGGGGSEN<br>VLTQSPSSMSVSVGDRVTIACSASSSVPYMHWLQQKPG<br>KSPKLLIYSTSNLASGVPSRFSGSGSGTDYSLTISSVQ<br>PEDAATYYCQQRSSYPLTFGCGTKLEIKR | 19 |
| Anti-Digoxigenin (Fab-LC) | MEAPAQLLFLLLLWLPDTTGDIQMTQSPSSLSASVGDR<br>VTITCRASQDIKNYLNWYQQKPGKAPKLLIYYSSTLLS<br>GVPSRFSGSGSGTDFTLTISSLQPEDFATYYCQQSITL<br>PPTFGGGTKVEIKRTVAAPSVFIFPPSDEQLKSGTASV<br>VCLLNNFYPREAKVQWKVDNALQSGNSQESVTEQDSKD<br>STYSLSSTLTLSKADYEKHKVYACEVTHQGLSSPVTKS<br>FNRGEC | 20 |

The following sequences are polynucleotides of the invention encoding amino acid sequences comprised in the antigen binding molecules of the invention.

| Description | Nucleotide sequence | Seq. ID # |
|---|---|---|
| VHCH1-CMP-Flag DR5 clone 2A11 | ATGGGATGGAGCTGTATCATCCTCTTCTTGGTAGCAACAGCTA<br>CCGGTGTGCATTCCGAGGTGCAATTGTTGGAGTCTGGGGGAGG<br>CTTGGTACAGCCTGGGGGGTCCCTGAGACTCTCCTGTGCAGCC<br>TCCGGATTCACCTTTAGCAGTTATGCCATGAGCTGGGTCCGCC<br>AGGCTCCAGGGAAGGGGCTGGAGTGGGTCTCAGCTATTAGTGG<br>TAGTGGTGGTAGCACATACTACGCAGACTCCGTGAAGGGCCGG<br>TTCACCATCTCCAGAGACAATTCCAAGAACACGCTGTATCTGC<br>AGATGAACAGCCTGAGAGCCGAGGACACGGCCGTATATTACTG<br>TGCGCGTGGTCCGTACGGTCGTTACGCTGCTCTGGACTACTGG<br>GGCCAAGGAACCCTGGTCACCGTCTCGAGTGCTAGCACAAAGG<br>GACCTAGCGTGTTCCCCCTGGCCCCCAGCAGCAAGTCTACATC<br>TGGCGGAACAGCCGCCCTGGGCTGCCTCGTGAAGGACTACTTT<br>CCCGAGCCCGTGACCGTGTCCTGGAACTCTGGCGCTCTGACAA<br>GCGGCGTGCACACCTTTCCAGCCGTGCTGCAGAGCAGCGGCCT<br>GTACTCTCTGAGCAGCGTCGTGACAGTGCCCAGCAGCTCTCTG<br>GGCACCCAGACCTACATCTGCAACGTGAACCACAAGCCCAGCA<br>ACACCAAGGTGGACAAGAAGGTGGAACCCAAGAGCTGCGACGG<br>CGGAGGGGGATCTGGCGGCGGAGGATCCGAAGAAGATCCTTGC<br>GCCTGCGAGAGCCTCGTGAAATTCCAGGCCAAGGTGGAAGGAC<br>TGCTGCAGGCCCTGACCCGGAAACTGGAAGCCGTGTCCAAGCG<br>GCTGGCCATCCTGGAAAACACCGTGGTGGCCAGCGACTACAAG<br>GACGACGACGACAAGTCCGGA | 11 |
| VHCH1-CMP-Flag DR5 clone 5E11 | ATGGGATGGAGCTGTATCATCCTCTTCTTGGTAGCAACAGCTA<br>CCGGTGTGCATTCCGAGGTGCAATTGTTGGAGTCTGGGGGAGG<br>CTTGGTACAGCCTGGGGGGTCCCTGAGACTCTCCTGTGCAGCC<br>TCCGGATTCACCTTTAGCAGTTATGCCATGAGCTGGGTCCGCC<br>AGGCTCCAGGGAAGGGGCTGGAGTGGGTCTCAGCTATTAGTGG<br>TAGTGGTGGTAGCACATACTACGCAGACTCCGTGAAGGGCCGG<br>TTCACCATCTCCAGAGACAATTCCAAGAACACGCTGTATCTGC<br>AGATGAACAGCCTGAGAGCCGAGGACACGGCCGTATATTACTG<br>TGCGAAAGGGGTGAGGGTGTCTTTTGACTACTGGGGCCAAGGA<br>ACCCTGGTCACCGTCTCGAGTGCTAGCACAAAGGGACCTAGCG<br>TGTTCCCCCTGGCCCCAGCAGCAAGTCTACATCTGGCGGAAC<br>AGCCGCCCTGGGCTGCCTCGTGAAGGACTACTTTCCCGAGCCC<br>GTGACCGTGTCCTGGAACTCTGGCGCTCTGACAAGCGGCGTGC<br>ACACCTTTCCAGCCGTGCTGCAGAGCAGCGGCCTGTACTCTCT | 12 |

-continued

| Description | Nucleotide sequence | Seq. ID # |
|---|---|---|
| | GAGCAGCGTCGTGACAGTGCCCAGCAGCTCTCTGGGCACCCAG<br>ACCTACATCTGCAACGTGAACCACAAGCCCAGCAACACCAAGG<br>TGGACAAGAAGGTGGAACCCAAGAGCTGCGACGGCGGAGGGGG<br>ATCTGGCGGCGGAGGGATCCGAAGAAGATCCTTGCGCCTGCGAG<br>AGCCTCGTGAAATTCCAGGCCAAGGTGGAAGGACTGCTGCAGG<br>CCCTGACCCGGAAACTGGAAGCCGTGTCCAAGCGGCTGGCCAT<br>CCTGGAAAACACCGTGGTGGCCAGCGACTACAAGGACGACGAC<br>GACAAGTCCGGA | |
| 5E11_28H1<br>CrossFab<br>VHCH1-CMP-<br>VHCL | GAGGTGCAATTGTTGGAGTCTGGGGGAGGCTTGGTACAGCCTG<br>GGGGGTCCCTGAGACTCTCCTGTGCAGCCTCCGGATTCACCTT<br>TAGCAGTTATGCCATGAGCTGGGTCCGCCAGGCTCCAGGGAAG<br>GGGCTGGAGTGGGTCTCAGCTATTAGTGGTAGTGGTGGTAGCA<br>CATACTACGCAGACTCCGTGAAGGGCCGGTTCACCATCTCCAG<br>AGACAATTCCAAGAACACGCTGTATCTGCAGATGAACAGCCTG<br>AGAGCCGAGGACACGGCCGTATATTACTGTGCGAAAGGGGTGA<br>GGGTGTCTTTTGACTACTGGGGCCAAGGAACCCTGGTCACCGT<br>CTCGAGTGCTAGCACAAAGGGACCTAGCGTGTTCCCCCTGGCC<br>CCCAGCAGCAAGTCTACATCTGGCGGAACAGCCGCCCTGGGCT<br>GCCTCGTGAAGGACTACTTTCCCGAGCCCGTGACCGTGTCCTG<br>GAACTCTGGCGCTCTGACAAGCGGCGTGCACACCTTTCCAGCC<br>GTGCTGCAGAGCAGCGGCCTGTACTCTCTGAGCAGCGTCGTGA<br>CAGTGCCCAGCAGCTCTCTGGGCACCCAGACCTACATCTGCAA<br>CGTGAACCACAAGCCCAGCAACACCAAGGTGGACAAGAAGGTG<br>GAACCCAAGAGCTGCGACGGCGGAGGGGGATCTGGCGGCGGAG<br>GATCCGAAGAAGATCCTTGCGCCTGCGAGAGCCTCGTGAAATT<br>CCAGGCCAAGGTGGAAGGACTGCTGCAGGCCCTGACCCGGAAA<br>CTGGAAGCCGTGTCCAAGCGGCTGGCCATCCTGGAAAACACCG<br>TGGTGGCCAGCGACTACAAGGACGACGACGACAAGTCCGGAGG<br>CGGCGGAAGCGGAGGAGGAGGATCCGGAGGAGGGGAAGTGGC<br>GGCGGAGGATCTGAGGTGCAGCTGCTGGAATCCGGCGGAGGCC<br>TGGTGCAGCCTGGCGGATCTCTGAGACTGTCCTGCGCCGCCTC<br>CGGCTTCACCTTCTCCTCCCACGCCATGTCCTGGGTCCGACAG<br>GCTCCTGGCAAAGGCCTGGAATGGGTGTCCGCCATCTGGGCCT<br>CCGGCGAGCAGTACTACGCCGACTCTGTGAAGGGCCGGTTCAC<br>CATCTCCCGGGACAACTCCAAGAACACCCTGTACCTGCAGATG<br>AACTCCCTGCGGGCCGAGGACACCGCCGTGTACTACTGTGCCA<br>AGGGCTGGCTGGGCAACTTCGACTACTGGGGCCAGGGCACCCT<br>GGTCACCGTGTCCAGCGCTAGCGTGGCCGCTCCCAGCGTGTTC<br>ATCTTCCCACCCAGCGACGAGCAGCTGAAGTCCGGCACAGCCA<br>GCGTGGTGTGCCTGCTGAACAACTTCTACCCCCGCGAGGCCAA<br>GGTGCAGTGGAAGGTGGACAACGCCCTGCAGAGCGGCAACAGC<br>CAGGAATCCGTGACCGAGCAGGACAGCAAGGACTCCACCTACA<br>GCCTGAGCAGCACCCTGACCCTGAGCAAGGCCGACTACGAGAA<br>GCACAAGGTGTACGCCTGCGAAGTGACCCACCAGGGCCTGTCC<br>AGCCCCGTGACCAAGAGCTTCAACCGGGGCGAGTGC | 13 |
| 5E11_28H1 scFv<br>VHCH1-CMP-<br>VHVL | GAGGTGCAATTGTTGGAGTCTGGGGGAGGCTTGGTACAGCCTG<br>GGGGGTCCCTGAGACTCTCCTGTGCAGCCTCCGGATTCACCTT<br>TAGCAGTTATGCCATGAGCTGGGTCCGCCAGGCTCCAGGGAAG<br>GGGCTGGAGTGGGTCTCAGCTATTAGTGGTAGTGGTGGTAGCA<br>CATACTACGCAGACTCCGTGAAGGGCCGGTTCACCATCTCCAG<br>AGACAATTCCAAGAACACGCTGTATCTGCAGATGAACAGCCTG<br>AGAGCCGAGGACACGGCCGTATATTACTGTGCGAAAGGGGTGA<br>GGGTGTCTTTTGACTACTGGGGCCAAGGAACCCTGGTCACCGT<br>CTCGAGTGCTAGCACAAAGGGACCTAGCGTGTTCCCCCTGGCC<br>CCCAGCAGCAAGTCTACATCTGGCGGAACAGCCGCCCTGGGCT<br>GCCTCGTGAAGGACTACTTTCCCGAGCCCGTGACCGTGTCCTG<br>GAACTCTGGCGCTCTGACAAGCGGCGTGCACACCTTTCCAGCC<br>GTGCTGCAGAGCAGCGGCCTGTACTCTCTGAGCAGCGTCGTGA<br>CAGTGCCCAGCAGCTCTCTGGGCACCCAGACCTACATCTGCAA<br>CGTGAACCACAAGCCCAGCAACACCAAGGTGGACAAGAAGGTG<br>GAACCCAAGAGCTGCGACGGCGGAGGGGGATCTGGCGGCGGAG<br>GATCCGAGGAAGATCCTTGCGCCTGCGAGAGCCTCGTGAAGTT<br>CCAGGCCAAGGTGGAAGGACTGCTGCAGGCCCTGACCCGGAAA<br>CTGGAAGCCGTGTCCAAGCGGCTGGCCATCCTGGAAAACACCG<br>TGGTGTCCGGAGGCGGGGGTAGCGGCGGAGGGGGCTCTGGCGG<br>TGGCGGGTCTGGAGGCGGGGGTTCAGAAGTGCAGCTGCTGGAA<br>TCTGGCGGCGGACTGGTGCAGCCTGGCGGATCTCTGAGACTGA<br>GCTGTGCCGCCAGCGGCTTCACCTTTAGCAGCCACGCCATGAG<br>CTGGGTGCGCCAGGCCCCTGGAAAGTGCCTGGAATGGGTGTCC<br>GCCATCTGGGCCAGCGGCGAGCAGTACTACGCCGATAGCGTGA<br>AGGGCCGGTTCACCATCAGCCGGGACAACAGCAAGAACACCCT<br>GTACCTGCAGATGAACAGCCTGCGGGCCGAGGACACCGCCGTG<br>TACTATTGTGCCAAGGGCTGGCTGGGCAACTTCGACTATTGGG<br>GCCAGGGCACCCTCGTGACCGTGTCTAGCGGAGGGGCGGAAG<br>TGGTGGCGGGGAAGCGGCGGGGGTGGCAGCGGAGGGGCGGA | 14 |

| Description | Nucleotide sequence | Seq. ID # |
|---|---|---|
| | TCTGAAATTGTGCTGACCCAGAGCCCTGGCACCCTGAGCCTGT<br>CTCCAGGCGAAAGAGCCACACTGAGCTGCAGAGCCAGCCAGAG<br>CGTGTCCAGAAGCTACCTGGCCTGGTATCAGCAGAAGCCCGGA<br>CAGGCCCCCAGACTGCTGATCATCGGCGCCTCTACAAGAGCCA<br>CCGGCATCCCCGATAGATTCAGCGGCTCTGGCAGCGGCACCGA<br>CTTCACCCTGACCATCAGCAGACTGGAACCCGAGGACTTTGCC<br>GTGTATTACTGCCAGCAGGGCCAAGTGATCCCCCCCACCTTTG<br>GCTGTGGCACAAAGGTGGAAATCAAA | |
| CMP-28H1<br>CrossFab | GGATCCGAGGAAGATCCTTGCGCCTGCGAGAGCCTCGTGAAGT<br>TCCAGGCCAAGGTGGAAGGACTGCTGCAGGCCCTGACCCGGAA<br>ACTGGAAGCCGTGTCCAAGCGGCTGGCCATCCTGGAAAACACC<br>GTGGTGTCCGGAGGCGGCGGAAGCGGAGGAGGAGGATCCGGAG<br>AGGGGGGAAGTGGCGGCGGAGGATCTGAGGTGCAGCTGCTGGA<br>ATCCGGCGGAGGCCTGGTGCAGCCTGGCGGATCTCTGAGACTG<br>TCCTGCGCCGCCTCCGGCTTCACCTTCTCCTCCCACGCCATGT<br>CCTGGGTCCGACAGGCTCCTGGCAAAGGCCTGGAATGGGTGTC<br>CGCCATCTGGGCCTCCGGCGAGCAGTACTACGCCGACTCTGTG<br>AAGGGCCGGTTCACCATCTCCCGGGACAACTCCAAGAACACCC<br>TGTACCTGCAGATGAACTCCCTGCGGGCCGAGGACACCGCCGT<br>GTACTACTGTGCCAAGGGCTGGCTGGGCAACTTCGACTACTGG<br>GGCCAGGGCACCCTGGTCACCGTGTCCAGCGCTAGCGTGGCCG<br>CTCCCAGCGTGTTCATCTTCCCACCCAGCGACGAGCAGCTGAA<br>GTCCGGCACAGCCAGCGTGGTGTGCCTGCTGAACAACTTCTAC<br>CCCCGCGAGGCCAAGGTGCAGTGGAAGGTGGACAACGCCCTGC<br>AGAGCGGCAACAGCCAGGAATCCGTGACCGAGCAGGACAGCAA<br>GGACTCCACCTACAGCCTGAGCAGCACCCTGACCCTGAGCAAG<br>GCCGACTACGAGAAGCACAAGGTGTACGCCTGCGAAGTGACCC<br>ACCAGGGCCTGTCCAGCCCCGTGACCAAGAGCTTCAACCGGGG<br>CGAGTGC | 15 |
| VLCL<br>DR5 clone 2A11 | ATGGGATGGAGCTGTATCATCCTCTTCTTGGTAGCAACAGCTA<br>CCGGTGTGCATTCCGACATCCAGATGACCCAGAGCCCCAGCAG<br>CCTGAGCGCCAGCGTGGGCGACAGAGTGACCATCACCTGCAGC<br>GCCAGCCAGGGCATCCGGAACTACCTGAACTGGTATCAGCAGA<br>AGCCCGGCAAGGCCCCCAAGCTGCTGATCTACTACACCAGCAG<br>CCTGCACAGCGGCGTGCCTAGCCGGTTTAGCGGCAGCGGCTCC<br>GGCACCGACTTCACCCTGACCATTAGCTCCCTGCAGCCCGAGG<br>ACTTCGCCACCTACTACTGCCAGCAGTACAGCAAGCTGCCCTG<br>GACCTTCGGCCAGGGAACAAAGGTGGAGATCAAGCGTACGGTG<br>GCTGCACCATCTGTCTTCATCTTCCCGCCATCTGATGAGCAGT<br>TGAAATCTGGAACTGCCTCTGTTGTGTGCCTGCTGAATAACTT<br>CTATCCCAGAGAGGCCAAAGTACAGTGGAAGGTGGATAACGCC<br>CTCCAATCGGGTAACTCCCAGGAGAGTGTCACAGAGCAGGACA<br>GCAAGGACAGCACCTACAGCCTCAGCAGCACCCTGACGCTGAG<br>CAAAGCAGACTACGAGAAACACAAAGTCTACGCCTGCGAAGTC<br>ACCCATCAGGGCCTGAGCTCGCCCGTCACAAAGAGCTTCAACA<br>GGGGAGAGTGT | 16 |
| VLCL<br>DR5 clone 5E11 | ATGGGATGGAGCTGTATCATCCTCTTCTTGGTAGCAACAGCTA<br>CCGGTGTGCATTCCGAAATCGTGTTAACGCAGTCTCCAGGCAC<br>CCTGTCTTTGTCTCCAGGGGAAAGAGCCACCCTCTCTTGCAGG<br>GCCAGTCAGAGTGTTAGCAGCAGCTACTTAGCCTGGTACCAGC<br>AGAAACCTGGCCAGGCTCCCAGGCTCCTCATCTATGGAGCATC<br>CAGCAGGGCCACTGGCATCCCAGACAGGTTCAGTGGCAGTGGA<br>TCCGGGACAGACTTCACTCTCACCATCAGCAGACTGGAGCCTG<br>AAGATTTTGCAGTGTATTACTGTCAGCAGGGTACTACTCATCC<br>CATTACGTTCGGCCAGGGGACCAAAGTGGAAATCAAACGTACG<br>GTGGCTGCACCATCTGTCTTCATCTTCCCGCCATCTGATGAGC<br>AGTTGAAATCTGGAACTGCCTCTGTTGTGTGCCTGCTGAATAA<br>CTTCTATCCCAGAGAGGCCAAAGTACAGTGGAAGGTGGATAAC<br>GCCCTCCAATCGGGTAACTCCCAGGAGAGTGTCACAGAGCAGG<br>ACAGCAAGGACAGCACCTACAGCCTCAGCAGCACCCTGACGCT<br>GAGCAAAGCAGACTACGAGAAACACAAAGTCTACGCCTGCGAA<br>GTCACCCATCAGGGCCTGAGCTCGCCCGTCACAAAGAGCTTCA<br>ACAGGGGAGAGTGT | 17 |
| VLCH1<br>FAP clone 28H1 | GAGATCGTGCTGACCCAGTCTCCCGGCACCCTGAGCCTGAGCC<br>CTGGCGAGAGAGCCACCCTGAGCTGCAGAGCCAGCCAGAGCGT<br>GAGCCGGAGCTACCTGGCCTGGTATCAGCAGAAGCCCGGCCAG<br>GCCCCCAGACTGCTGATCATCGGCGCCAGCACCCGGGCCACCG<br>GCATCCCCGATAGATTCAGCGGCAGCGGCTCCGGCACCGACTT<br>CACCCTGACCATCAGCCGGCTGGAACCCGAGGACTTCGCCGTG<br>TACTACTGCCAGCAGGGCCAGGTGATCCCCCCCACCTTCGGCC<br>AGGGCACCAAGGTGGAAATCAAGAGCTCCGCTAGCACCAAGGG<br>CCCCTCCGTGTTTCCTCTGGCCCCCAGCAGCAAGAGCACCTCT<br>GGCGGAACAGCCGCCCTGGGCTGCCTGGTGAAAGACTACTTCC | 18 |

-continued

| Description | Nucleotide sequence | Seq. ID # |
|---|---|---|
| | CCGAGCCCGTGACCGTGTCCTGGAACTCTGGCGCCCTGACCAG<br>CGGCGTGCACACCTTTCCAGCCGTGCTGCAGAGCAGCGGCCTG<br>TACTCCCTGAGCAGCGTGGTGACAGTGCCCTCCAGCAGCCTGG<br>GCACCCAGACCTACATCTGCAACGTGAACCACAAGCCCAGCAA<br>CACCAAAGTGGACAAGAAGGTGGAACCCAAGAGCTGCGAC | |
| Anti-<br>Digoxigenin(Fab-<br>HC)-CMP-anti-<br>CEA(scFv) | ATGGGCTGGTCCTGCATCATCCTGTTTCTGGTGGCCACCGCTA<br>CCGGCGTCCATAGCCAGGTGCAGCTGGTGGAAAGCGGCGGAGG<br>CCTGGTGAAACCGGGAGGCTCTCTGAGACTGTCTTGCGCTGCG<br>AGCGGCTTTACCTTTAGCGATTATGCGATGAGCTGGATTCGCC<br>AGGCGCCGGGCAAAGGCCTGGAATGGGTGAGCAGCATTAACAT<br>TGGCGCGACCTATATTTATTATGCGGATAGCGTGAAAGGCCGC<br>TTTACCATTAGCCGCGATAACGCGAAAAACAGCCTGTATCTGC<br>AGATGAATAGCCTCAGAGCGGAAGATACAGCGGTGTATTATTG<br>CGCGCGCCCGGGCAGCCCGTATGAATATGATAAAGCGTATTAT<br>AGCATGGCGTATTGGGGCCAGGGCACCACCGTGACAGTGAGCA<br>GCGCGTCGACTAAGGGCCCTTCAGTTTTTCCACTCGCCCCCAG<br>TAGCAAGTCCACATCTGGGGGTACCGCTGCCCTGGGCTGCCTT<br>GTGAAAGACTATTTCCCTGAACCAGTCACTGTGTCATGGAATA<br>GCGGAGCCCTGACCTCCGGTGTACACACATTCCCCGCTGTGTT<br>GCAGTCTAGTGGCCTGTACAGCCTCTCCTCTGTTGTGACCGTC<br>CCTTCAAGCTCCCTGGGGACACAGACCTATATCTGTAACGTGA<br>ATCATAAGCCATCTAACACTAAGGTAGATAAAAAAGTGGAGCC<br>CAAGAGTTGCGACAAAACACACGGAGGTGGTGGATCGGCGGA<br>GGTGGCAGTGAGGAAGACCCCTGCGCCTGTGAGAGCCTGGTGA<br>AGTTCCAGGCTAAAGTCGAGGGCCTCCTGCAGGCACTTACCAG<br>GAAGCTGGAAGCCGTGTCCAAGAGACTCGCTATCCTGGAGAAC<br>ACAGTCGTGGGCGGAGGCGGTTCAGGGGGAGGCGGTAGCCAAG<br>TGAAGCTGGAGCAGAGCGGCGCCGAAGTCGTGAAACCCGGGGC<br>TTCCGTCAAGCTCTCTTGCAAGGCATCAGGATTCAACATCAAA<br>GACAGCTACATGCACTGGCTGAGGCAGGCCCTGGTCAGTGCC<br>TTGAGTGGATTGGCTGGATCGATCCAGAGAATGGCGACACCGA<br>ATATGCCCCCAAGTTTCAAGGAAAGGCTACATTCACCACTGAT<br>ACATCCGCAAACACCGCCTACCTGGGTCTCTCAAGTCTGCGCC<br>CTGAGGACACTGCTGTGTATTACTGTAATGAGGGCACCCCAAC<br>AGGGCCCTACTATTTTGACTACTGGGGACAGGGCACCTTGGTT<br>ACAGTGAGCTCCGGGGGAGGCGGTTCCGGGGGCGGAGGTTCTG<br>GGGGCGGAGGTTCTGGCGGGGAGGCTCAGAGAACGTGCTGAC<br>CCAGAGCCCCTCCTCTATGTCAGTCAGCGTGGGCGACAGGGTC<br>ACAATCGCCTGCTCCGCTTCTAGTAGCGTGCCTTACATGCACT<br>GGCTCCAGCAGAAGCCAGGGAAATCCCCCAAGCTGCTTATTTA<br>TTCTACCTCAAATCTGGCAAGCGGAGTTCCTAGCAGATTCTCT<br>GGCAGTGGTAGCGGGACTGATTACTCCCTCACAATCTCAAGTG<br>TGCAGCCAGAAGACGCCGCTACCTATTACTGTCAACAGCGCAG<br>CTCCTACCCCCTGACTTTTGGCTGTGGCACCAAGTTGGAGATT<br>AAACGGTGA | 21 |
| Anti-<br>Digoxigenin(Fab-<br>LC) | ATGGAAGCCCCAGCTCAGCTTCTCTTCCTCCTGCTACTCTGGC<br>TCCCAGATACCACCGGAGATATTCAGATGACCCAGAGCCCGAG<br>CAGCCTGAGCGCGAGCGTGGGCGATCGCGTGACCATTACCTGC<br>CGCGCGAGCCAGGATATTAAAAACTATCTGAACTGGTATCAGC<br>AGAAACCGGGCAAAGCGCCGAAACTGCTGATTTATTATAGCAG<br>CACCCTGCTGAGCGGCGTGCCGAGCCGCTTTAGCGGCAGCGGC<br>AGCGGCACCGATTTTACCCTGACCATTAGCAGCCTGCAGCCGG<br>AAGATTTTGCGACCTATTATTGCCAGCAGAGCATTACCCTGCC<br>GCCGACCTTTGGCGGCGGCACCAAAGTGGAAATTAAACGTACG<br>GTGGCTGCACCATCTGTCTTCATCTTCCCGCCATCTGATGAGC<br>AGTTGAAATCTGGAACTGCCTCTGTTGTGTGCCTGCTGAATAA<br>CTTCTATCCCAGAGAGGCCAAAGTACAGTGGAAGGTGGATAAC<br>GCCCTCCAATCGGGTAACTCCCAGGAGAGTGTCACAGAGCAGG<br>ACAGCAAGGACAGCACCTACAGCCTCAGCAGCACCCTGACGCT<br>GAGCAAAGCAGACTACGAGAAACACAAAGTCTACGCCTGCGAA<br>GTCACCCATCAGGGCCTGAGCTCGCCCGTCACAAAGAGCTTCA<br>ACAGGGGAGAGTGTTAG | 22 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A trimeric antigen binding molecule comprising three fusion polypeptides, each comprising at least one antigen binding moiety fused to a trimerization domain consisting of SEQ ID NO:2, wherein said trimerization domain is capable of mediating stable association of the trimeric antigen binding molecule, and wherein said antigen binding moiety is a Fab molecule.

2. The trimeric antigen binding molecule of claim 1, wherein the three fusion polypeptides are linked by disulfide bonds.

3. The trimeric antigen binding molecule of claim 1, wherein said fusion polypeptides each comprise one antigen binding moiety fused to said trimerization domain.

4. The trimeric antigen binding molecule of claim 1, wherein said Fab molecule is fused at the C-terminal amino acid of the Fab heavy chain to the N-terminal amino acid of said trimerization domain.

5. The trimeric antigen binding molecule of claim 1, wherein said antigen binding moiety is capable of specific binding to a cell surface antigen.

6. The trimeric antigen binding molecule of claim 5, wherein said cell surface antigen is a tumor cell antigen.

7. The trimeric antigen binding molecule of claim 1, wherein each of said fusion polypeptides comprises a first and a second antigen binding moiety fused to said trimerization domain.

8. The trimeric antigen binding molecule of claim 7, wherein the first antigen binding moiety is fused to the N-terminal amino acid of said trimerization domain, and wherein the second antigen binding moiety is fused to the C-terminal amino acid of said trimerization domain.

9. The trimeric antigen binding molecule of claim 7, wherein the first antigen binding moiety is a Fab molecule and the second antigen binding moiety is a scFv molecule or a crossover Fab molecule.

10. The trimeric antigen binding molecule of claim 9, wherein said Fab molecule is fused at the N-terminal amino acid of the Fab heavy chain to the C-terminal amino acid of said trimerization domain.

11. The trimeric antigen binding molecule of claim 7, wherein the first or the second antigen binding moiety is capable of specific binding to a cell surface antigen.

12. The trimeric antigen binding molecule of claim 7, wherein the first or the second antigen binding moiety is capable of specific binding to a hapten.

13. The trimeric antigen binding molecule of claim 1, consisting of three fusion polypeptides each consisting of an antigen binding moiety fused to said trimerization domain.

14. The trimeric antigen binding molecule of claim 7, consisting of three fusion polypeptides each consisting of a first and a second antigen binding moiety fused to said trimerization domain.

15. The trimeric antigen binding molecule of claim 1, wherein said three fusion polypeptides are identical.

16. A pharmaceutical composition comprising the trimeric antigen binding molecule of claim 1 and a pharmaceutically acceptable carrier.

17. The trimeric antigen binding molecule of claim 4, wherein said Fab molecule is fused at the C-terminal amino acid of the Fab heavy chain to the N-terminal amino acid of said trimerization domain through a peptide linker.

18. The trimeric antigen binding molecule of claim 8, wherein the first antigen binding moiety is fused to the N-terminal amino acid of said trimerization domain through a peptide linker.

19. The trimeric antigen binding molecule of claim 8, wherein the second antigen binding moiety is fused to the C-terminal amino acid of said trimerization domain through a peptide linker.

20. The trimeric antigen binding molecule of claim 18, wherein the second antigen binding moiety is fused to the C-terminal amino acid of said trimerization domain through a peptide linker.

21. The trimeric antigen binding molecule of claim 10, wherein said Fab molecule is fused at the N-terminal amino acid of the Fab heavy chain to the C-terminal amino acid of said trimerization domain through a peptide linker.

22. The trimeric antigen binding molecule of claim 13, consisting of three fusion polypeptides each consisting of an antigen binding moiety fused to said trimerization domain through a peptide linker.

23. The trimeric antigen binding molecule of claim 14, consisting of three fusion polypeptides each consisting of a first and a second antigen binding moiety fused to said trimerization domain through a peptide linker.

\* \* \* \* \*